United States Patent
Zode

(10) Patent No.: US 10,774,328 B2
(45) Date of Patent: Sep. 15, 2020

(54) TREATMENT FOR GLAUCOMA AND OTHER EYE DISEASES

(71) Applicant: University of North Texas Health Science Center at Fort Worth, Fort Worth, TX (US)

(72) Inventor: Gulab Zode, Fort Worth, TX (US)

(73) Assignee: UNIVERSITY OF NORTH TEXAS HEALTH SCIENCE CENTER AT FORT WORTH, Fort Worth, TX (US)

(*) Notice: Subject to any disclaimer, the term of this patent is extended or adjusted under 35 U.S.C. 154(b) by 0 days.

(21) Appl. No.: 16/317,473

(22) PCT Filed: Jul. 11, 2017

(86) PCT No.: PCT/US2017/041539
§ 371 (c)(1),
(2) Date: Jan. 11, 2019

(87) PCT Pub. No.: WO2018/013568
PCT Pub. Date: Jan. 18, 2018

(65) Prior Publication Data
US 2019/0225966 A1   Jul. 25, 2019

Related U.S. Application Data

(60) Provisional application No. 62/360,575, filed on Jul. 11, 2016.

(51) Int. Cl.

| | |
|---|---|
| C07H 21/02 | (2006.01) |
| C07H 21/04 | (2006.01) |
| C12N 15/113 | (2010.01) |
| A61K 38/17 | (2006.01) |
| A61K 45/06 | (2006.01) |
| A61K 31/436 | (2006.01) |
| C07K 14/47 | (2006.01) |
| A61K 31/5377 | (2006.01) |
| A61K 31/4745 | (2006.01) |
| A61K 31/155 | (2006.01) |
| A61P 27/02 | (2006.01) |

(52) U.S. Cl.
CPC .......... *C12N 15/113* (2013.01); *A61K 31/155* (2013.01); *A61K 31/436* (2013.01); *A61K 31/4745* (2013.01); *A61K 31/5377* (2013.01); *A61K 38/1709* (2013.01); *A61K 45/06* (2013.01); *A61P 27/02* (2018.01); *C07K 14/4705* (2013.01); *C12N 2310/111* (2013.01); *C12N 2310/141* (2013.01); *C12N 2310/20* (2017.05); *C12N 2320/10* (2013.01)

(58) Field of Classification Search
CPC ............................ C12N 15/115; A61K 31/713
See application file for complete search history.

(56) References Cited

U.S. PATENT DOCUMENTS

| | | | |
|---|---|---|---|
| 2012/0101160 A1* | 4/2012 | Shepard | A61K 31/10 514/556 |
| 2014/0315942 A1* | 10/2014 | Kaspar | A61K 9/0014 514/291 |
| 2016/0000753 A1 | 1/2016 | Rinsch et al. | |

FOREIGN PATENT DOCUMENTS

| | | | | |
|---|---|---|---|---|
| EP | 3481411 A1 | | 5/2019 | |
| WO | WO 2014/110006 A1 * | | 7/2014 | ........... C12N 15/113 |
| WO | 2018013568 A1 | | 1/2018 | |

OTHER PUBLICATIONS

Sano et al. (Biochim Biophys Acta, 2013, 1833(12), 3460-3470).*
Peters et al. (IOVS, 2015, vol. 56, No. 6, 3860-3868).*
Shoji-Kawata et al. (Nature, 2013, 494(7436), 201-206).*
PCT/US2017/041539 PCT International Search Report and Written Opinion of Korean Intellectual Property Office dated Oct. 25, 2017, 21 pp.
Sano, R., et al., "ER stress-induced cell death mechanisms," Biochimica et Biophysica Acta, 1833, Jul. 10, 2013, pp. 3460-3470.
Zhang, Q., et al., "Zebrafish genome targeting with CRISPR-Cas9 endonuclease system at the nmnat1 locus," ARVO Annual Meeting Abstract, Apr. 2014, Abstract only.
Peters, et al. "Increased Endoplasmic Reticulum Stress in Human Glaucomatous Trabecular Meshwork Cells and Tissues" Invest Ophthalmol Vis Sci. (submitted Dec. 8, 2014) 2015;56(6):3860-8.
Renna, et al. "Chemical inducers of autophagy that enhance the clearance of mutant proteins in neurodegenerative diseases" J Biol Chem. Feb. 10, 2010;285(15)11061-7.
Sarkar, et al. "Trehalose, a novel mTOR-independent autophagy enhancer, accelerates the clearance of mutant huntingtin and alpha-synuclein" J Biol Chem. Feb. 23, 2007;282(8):5641-52.
Shoji-Kawata, et al. "Identification of a candidate therapeutic autophagy-inducing peptide" Nature. Feb. 14, 2013;494(7436):201-6.
Wang, et al. "Noninvasive measurement of rodent intraocular pressure with a rebound tonometer" Invest Ophthalmol Vis Sci., Dec. 2005;46(12):4617-21.
Zode, et al. "Reduction of ER stress via a chemical chaperone prevents disease phenotypes in a mouse model of primary open angle glaucoma" J Clin Invest. Sep. 2011;121(9):3542-53.

(Continued)

*Primary Examiner* — Amy H Bowman
(74) *Attorney, Agent, or Firm* — Edwin S. Flores; Daniel J. Chalker; Chalker Flores, LLP

(57) ABSTRACT

The present invention includes a composition and method for the treatment of an eye disease comprising a therapeutically effective amount of an autophagy stimulator that treats or slows the progression of the eye disease by enhancing or stimulating autophagy or correcting an autophagy deficiency.

11 Claims, 16 Drawing Sheets

Specification includes a Sequence Listing.

(56) References Cited

OTHER PUBLICATIONS

Zode, et al. "Topical ocular sodium 4-phenylbutyrate rescues glaucoma in a myocilin mouse model of primary open-angle glaucoma" Invest Ophthalmol Vis Sci., Mar. 2012;53(3):1557-65.

Zode, et al. "Ocular-specific ER stress reduction rescues glaucoma in murine glucocorticoid-induced glaucoma" J Clin Invest. May 2014;124(5):1956-65.

* cited by examiner

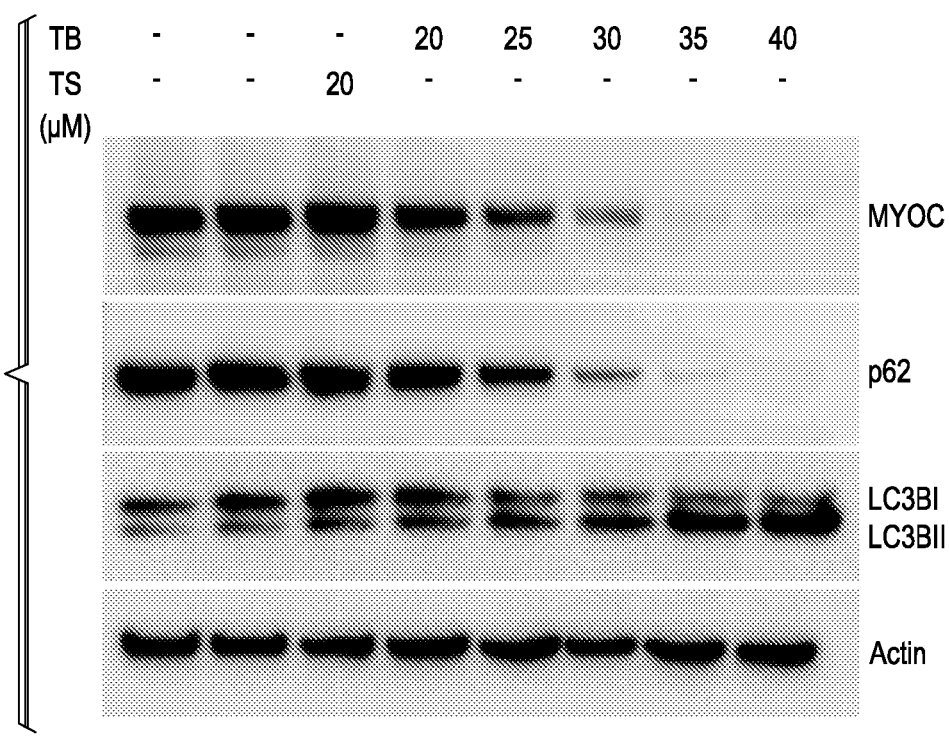
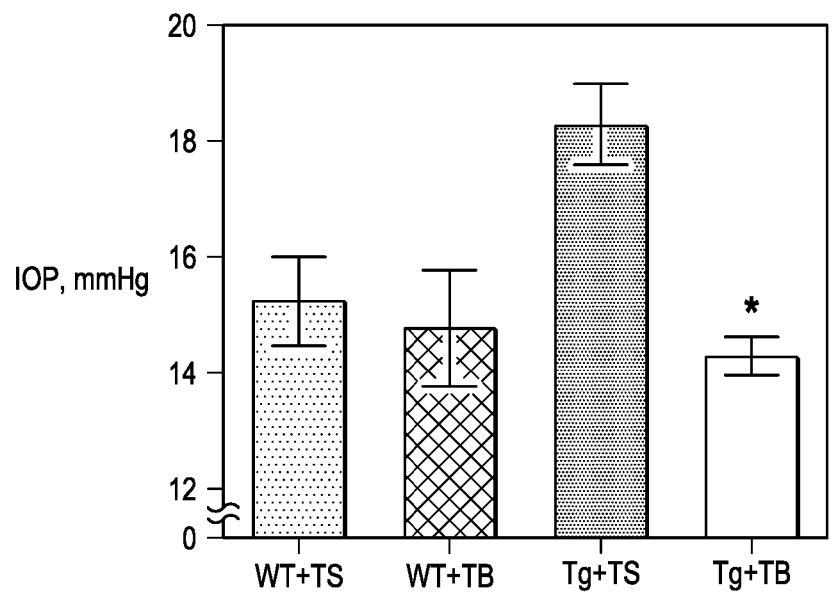

TREATMENT FOR GLAUCOMA AND OTHER EYE DISEASES

CROSS-REFERENCE TO RELATED APPLICATIONS

This application is the National Stage of International Application No. PCT/US2017/041539, filed on Jul. 11, 2017 claiming the priority of 62/360,575 filed on Jul. 11, 2016, the content of each of which is incorporated by reference herein.

STATEMENT OF FEDERALLY FUNDED RESEARCH

This invention was made with government support under EY022077 and EY026177 awarded by The National Institutes of Health. The government has certain rights in the invention.

TECHNICAL FIELD OF THE INVENTION

The present invention relates in general to the field of treatments for glaucoma and other eye diseases, and more particularly, to compositions and methods for enhancing autophagy to treat glaucoma and other eye diseases.

BACKGROUND OF THE INVENTION

Without limiting the scope of the invention, its background is described in connection with treatments for glaucoma.

Primary open angle glaucoma, a major cause of irreversible blindness, is often associated with elevated intraocular pressure (IOP) due to increased aqueous humor outflow resistance at the trabecular meshwork (TM). The pathological mechanisms leading to increased outflow resistance and IOP elevation are poorly understood.

Although the major pathology lies in the trabecular meshwork (increased outflow resistance elevates IOP in glaucoma), most current glaucoma treatments reduce IOP by reducing aqueous humor production by acting on ciliary body. In addition, these glaucoma treatments do not prevent blindness but merely halt progression of disease to some extent. Most glaucoma patients must undergo surgical procedures to reduce elevated IOP, which becomes expensive. Developing targeted treatments based on the understanding of TM pathology may improve clinical outcome and cure disease.

SUMMARY OF THE INVENTION

In one embodiment, the present invention includes a composition for the treatment of an eye disease comprising a therapeutically effective amount of an autophagy stimulator that treats or slows the progression of the eye disease by enhancing or stimulating autophagy or correcting an autophagy deficiency. In one aspect, the amount of the composition is sufficient to reduce at least one of protein misfolding, defective autophagy, or endoplasmic reticulum stress or increase autophagy. In another aspect, the autophagy stimulator is provided with a synergistic amount of a protein chaperone sufficient to treat or slow the progression of the eye disease. In another aspect, the eye disease comprises one or more symptoms selected from at least one of elevated intraocular pressure, increased aqueous humor outflow resistance at the trabecular meshwork, accumulation of misfolded proteins, or cell death. In another aspect, the composition is adapted for subcutaneous, cutaneous, intravitreal, intraocular, or ocular administration. In another aspect, the eye disease is caused by misfolded proteins, the loss of clearance of misfolded proteins, the accumulation of misfolded proteins, or a decrease in lysosomal activity. In another aspect, the eye disease is glaucoma, endoplasmic reticulum (ER) stress, autophagy deficiency, age-related macular degeneration (AMD), or diabetic retinopathy. In another aspect, the composition further comprises one or more pharmaceutically acceptable excipients. In another aspect, the autophagy stimulator is selected from at least one of: beclin 1 protein, Tat-beclin1 peptide (SEQ ID NO:1), Tat-Beclin 1 D11 (SEQ ID NO:10), trehalose, ISRIB, or an mTOR inhibitor. In another aspect, the mTOR inhibitor is at least one of rapamycin, temsirolimus, everolimus, KU-0063794, WYE-354, AZD8055, metformin, or Torin-2. In another aspect, the protein chaperone is 4-phenylbutyrate or a salt thereof, 1-deoxygalactonojirimycin or a salt thereof, isofagomine or a salt thereof, fagomine isomers or a salt thereof, dimethylsulfoxide (DMSO) or a salt thereof, tauroursodeoxycholic acid (TUDCA) or a salt thereof, ursodeoxycholic acid (UDCA) or a salt thereof, glycine betaine (betaine) or a salt thereof, glycerolphosphocholine (GPC) or a salt thereof, methylamines or a salt thereof, or trimethylamine N-oxide (TMAO), or a Histone deacetylase (DHAC inhibitor selected from Vorinostat, Romidepsin, Chidamide, Panobinostat, Valproic acid (e.g., Mg valproate), Belinostat, Mocetinostat (MGCD0103), Abexinostat (PCI-24781), Entinostat (MS-275), SB939, Resminostat (4SC-201), Givinostat (ITF2357), Quisinostat, HBI-8000, Kevetrin, CUDC-101, AR-42, CHR-2845, CHR-3996, 4SC-202, CG200745, ACY-1215, lenalidomide, ME-344, sulforaphane, and/or alpha-crystallin protein or a salt thereof. In another aspect, the autophagy stimulator is an inhibitor of a CHOP gene, an ATF4 gene, or both, comprising a gene knockdown construct selected from at least one of an siRNA, a miRNA, an shRNA, an antisense RNA, or an sgRNA, a programmable gene editing nuclease (CRISPR-Cas) knockdown of ATF4 and/or CHOP, or a gene editing or therapy that reduces expression of ATF4 and/or CHOP. In another aspect, the sgRNA construct targets an exon, intron, or exon/intron junction of a human CHOP gene and/or an exon, intron, or exon/intron junction of a human ATF4 gene. In another aspect, the sgRNA construct comprises (GACCACTCT-GTTTCCGTTTCC) (SEQ ID NO:4) and/or (AGGTCTCT-TAGATGATTACC) (SEQ ID NO:5).

In another embodiment, the present invention includes a composition for the treatment of an eye disease comprising a therapeutically effective amount of autophagy stimulator or enhancer adapted for treatment of the eye. In one aspect, the amount of the composition is sufficient to reduce at least one of protein misfolding, defective autophagy, or endoplasmic reticulum stress or increase autophagy. In another aspect, the eye disease comprises one or more symptoms selected from at least one of elevated intraocular pressure, increased aqueous humor outflow resistance at the trabecular meshwork, accumulation of misfolded proteins, or cell death. In another aspect, the composition is adapted for subcutaneous, cutaneous, intravitreal, intraocular, or ocular administration. In another aspect, the eye disease is caused by misfolded proteins, the loss of clearance of misfolded proteins, the accumulation of misfolded proteins, or a decrease in lysosomal activity. In another aspect, the eye disease is glaucoma, endoplasmic reticulum (ER) stress, autophagy deficiency, age-related macular degeneration (AMD), or diabetic retinopathy. In another aspect, the composition further comprises one or more pharmaceutically acceptable excipients. In another aspect, the autophagy stimulator is selected from at least one of: beclin 1 protein, Tat-beclin1 peptide (SEQ ID NO:1), Tat-Beclin 1 D11 (SEQ ID NO:10), trehalose, ISRIB, or an mTOR inhibitor. In another aspect, the mTOR inhibitor is at least one of rapamycin, temsirolimus, everolimus, KU-0063794, WYE-354, AZD8055, metformin, or Torin-2. In another aspect, the amount is sufficient to treat or reduce the progression of the eye disease. In another aspect, the composition further comprises a chemical protein chaperone in an amount that is synergistic for treating the eye disease.

In yet another embodiment, the present invention includes a composition for the treatment of an eye disease comprising a therapeutically effective amount of an inhibitor of a CHOP gene, an ATF4 gene, or both, comprising a gene knockdown construct selected from at least one of an siRNA, a miRNA, an shRNA, an antisense RNA, or an sgRNA, a programmable gene editing nuclease (CRISPR-Cas) knockdown of ATF4 and/or CHOP, or a gene editing or therapy that reduces expression of ATF4 and/or CHOP.

In another embodiment, the present invention includes a method of treating eye disease comprising: identifying a subject in need of treatment for an eye disease; and providing the subject with an effective amount of an autophagy stimulator sufficient to reduce at least one of defective autophagy, endoplasmic reticulum stress, or elevated intraocular pressure or increase autophagy. In one aspect, the eye disease comprises one or more symptoms selected from at least one of increased aqueous humor outflow resistance at the trabecular meshwork, accumulation of misfolded proteins, or cell death. In another aspect, the autophagy stimulator is selected from at least one of: beclin 1 protein, Tat-beclin1 peptide (SEQ ID NO:1), Tat-Beclin 1 D11 (SEQ ID NO:10), trehalose, ISRIB, or an mTOR inhibitor. In another aspect, the mTOR inhibitor is at least one of rapamycin, temsirolimus, everolimus, KU-0063794, WYE-354, AZD8055, metformin, or Torin-2. In another aspect, the method further comprises the step of providing the subject with a protein chaperone is selected from at least one of 4-phenylbutyrate or a salt thereof, 1-deoxygalactonojirimycin or a salt thereof, isofagomine or a salt thereof, fagomine isomers or a salt thereof, dimethylsulfoxide (DMSO) or a salt thereof, tauroursodeoxycholic acid (TUDCA) or a salt thereof, ursodeoxycholic acid (UDCA) or a salt thereof, glycine betaine (betaine) or a salt thereof, glycerolphosphocholine (GPC) or a salt thereof, methylamines or a salt thereof, or trimethylamine N-oxide (TMAO), or a Histone deacetylase (DHAC inhibitor selected from Vorinostat, Romidepsin, Chidamide, Panobinostat, Valproic acid (e.g., Mg valproate), Belinostat, Mocetinostat (MGCD0103), Abexinostat (PCI-24781), Entinostat (MS-275), SB939, Resminostat (4SC-201), Givinostat (ITF2357), Quisinostat, HBI-8000, Kevetrin, CUDC-101, AR-42, CHR-2845, CHR-3996, 4SC-202, CG200745, ACY-1215, lenalidomide, ME-344, sulforaphane, and/or alpha-crystallin protein or a salt thereof, in a synergistic amount with the autophagy stimulator sufficient to treat the eye disease. In another aspect, the method further comprises the step of providing the subject with a composition that comprises a synergistic amount of a protein chaperone and beclin1 protein, Tat-beclin1 peptide (SEQ ID NO:1), Tat-Beclin 1 D11 (SEQ ID NO:10), trehalose, ISRIB, rapamycin, temsirolimus, everolimus, KU-0063794, WYE-354, AZD8055, metformin, or Torin-2, or 4-phenylbutyrate or a salt thereof. In another aspect, the autophagy stimulator is adapted for subcutaneous, cutaneous, intravitreal, intraocular, or ocular administration. In another aspect, the method further comprises the step of determining that the subject has a an disease caused by misfolded proteins, the loss of clearance of misfolded proteins, the accumulation of misfolded proteins, or a decrease in lysosomal activity; and providing the subjected with the effective amount of a Tat-beclin1 peptide, Tat-beclin1 D11, trehalose, ISRIB, rapamycin, temsirolimus, everolimus, KU-0063794, WYE-354, AZD8055, metformin, Torin-2, and sodium 4-phenylbutyrate to treat the eye disease. In another aspect, the eye disease is glaucoma, endoplasmic reticulum (ER) stress, autophagy deficiency, age-related macular degeneration (AMD), or diabetic retinopathy. In another aspect, the autophagy stimulator is an inhibitor of a CHOP gene, an ATF4 gene, or both, comprising a gene knockdown construct selected from at least one of an siRNA, a miRNA, an shRNA, an antisense RNA, an sgRNA, a programmable gene editing nuclease (CRISPR-Cas) knockdown of ATF4 and/or CHOP, or a gene editing or therapy that reduces expression of ATF4 and/or CHOP. In another aspect, the sgRNA construct targets an exon, intron, or exon/intron junction of a human CHOP gene and/or an exon, intron, or exon/intron junction of a human ATF4 gene. In another aspect, the sgRNA construct comprises (GAC-CACTCTGTTTCCGTTTCC) (SEQ ID NO:4) and/or (AG-GTCTCTTAGATGATTACC) (SEQ ID NO:5).

In another embodiment, the present invention includes a method of lowering intraocular pressure in a mammal comprising administering to a subject in which such pressure lowering is desired, at least one of an effective amount of autophagy stimulator to achieve the desired lowering in pressure. In one aspect, the autophagy stimulator is selected from at least one of: beclin 1 protein, Tat-beclin1 peptide (SEQ ID NO:1), Tat-Beclin 1 D11 (SEQ ID NO:10), trehalose, ISRIB, or an mTOR inhibitor. In another aspect, the mTOR inhibitor is at least one of rapamycin, temsirolimus, everolimus, KU-0063794, WYE-354, AZD8055, metformin, or Torin-2. In another aspect, the method further comprises providing a synergistic amount of a protein chaperone for treating the eye disease. In another aspect, the protein chaperone is selected from at least one of 4-phenylbutyrate or a salt thereof, 1-deoxygalactonojirimycin or a salt thereof, isofagomine or a salt thereof, fagomine isomers or a salt thereof, dimethylsulfoxide (DMSO) or a salt thereof, tauroursodeoxycholic acid (TUDCA) or a salt thereof, ursodeoxycholic acid (UDCA) or a salt thereof, glycine betaine (betaine) or a salt thereof, glycerolphosphocholine (GPC) or a salt thereof, methylamines or a salt thereof, or trimethylamine N-oxide (TMAO), or a Histone deacetylase (DHAC inhibitor selected from Vorinostat, Romidepsin, Chidamide, Panobinostat, Valproic acid (e.g., Mg valproate), Belinostat, Mocetinostat (MGCD0103), Abexinostat (PCI-24781), Entinostat (MS-275), SB939, Resminostat (4SC-201), Givinostat (ITF2357), Quisinostat, HBI-8000, Kevetrin, CUDC-101, AR-42, CHR-2845, CHR-3996, 4SC-202, CG200745, ACY-1215, lenalidomide, ME-344, sulforaphane, and/or alpha-crystallin protein or a salt thereof. In another aspect, the autophagy stimulator is an inhibitor of a CHOP gene, an ATF4 gene, or both, comprising a gene knockdown construct selected from at least one of an siRNA, a miRNA, an shRNA, an antisense RNA, an sgRNA, a programmable gene editing nuclease (CRISPR-Cas) knockdown of ATF4 and/or CHOP, or a gene editing or therapy that reduces expression of ATF4 and/or CHOP. In another aspect, the sgRNA construct targets an exon, intron, or exon/intron junction of a human CHOP gene and/or an exon, intron, or exon/intron junction of a human ATF4 gene. In another aspect, the sgRNA construct comprises (GAC- CACTCTGTTTCCGTTTCC) (SEQ ID NO:4) and/or (AG-GTCTCTTAGATGATTACC) (SEQ ID NO:5).

In yet another embodiment, the present invention includes a method of evaluating a candidate drug believed to be useful in treating an eye disease, the method comprising: a) measuring at least one of protein misfolding, defective autophagy, or endoplasmic reticulum stress from tissue suspected of having an eye disease from a set of patients; b) administering the candidate drug to a first subset of the patients, and a placebo to a second subset of the patients; c) repeating step a) after the administration of the candidate drug or the placebo; and d) determining if the candidate drug reduces the level of protein misfolding, defective autophagy, or endoplasmic reticulum stress that is statistically significant as compared to any reduction occurring in the second subset of patients, wherein a statistically significant reduction indicates that the candidate drug is useful in treating the eye disease.

BRIEF DESCRIPTION OF THE DRAWINGS

For a more complete understanding of the features and advantages of the present invention, reference is now made to the detailed description of the invention along with the accompanying figures and in which:

FIG. 1A shows the result from treating TM-3 cells expressing mutant myocilin with various concentrations of TS or TB for 24 hours. The cell lysates were subjected to Western blot analysis for MYOC, p62 and LC3B (n=3). FIG. 1C is a graph that shows ocular hypertensiveTg-MYOCY437H mice treated with topical TB (5 mM) or TS (5 mM) eye drops 3 times daily for 4 days and measurements of WT (n=2) or Tg-MYOCY437H mice (n=3) show that TB treatment significantly reduces elevated IOP.

FIG. 5A is a graph that shows IOP elevation in different aged group Tg-MYOC$^{Y437H}$ mice compared to WT litter mates (n=8); FIG. 5B is a graph that shows reduced outflow facility in 7 months old Tg-MYOC$^{Y437H}$ mice compared to WT littermates (n=8-10); FIG. 5C is a graph that shows IOP elevation in 0.1% topical ocular dex treated mice compared to vehicle treated mice; and FIG. 5D is a graph that shows reduced outflow facility in dex treated mice compared to vehicle treated mice (p<0.005, *p<0.0001; vs veh-treated mice; n=8).

FIG. 6A is the anterior segment tissues of 6-month-old WT and Tg-MYOC$^{Y437H}$ (n=3WT & 3 Tg); FIG. 6B is the anterior segment tissues of vehicle (n=4) and Dex (n=4)-treated mice; and FIG. 6C is a post-mortem human normal and glaucomatous TM tissues lysates (n=4).

FIG. 7A is a Western blot of MYOC in conditioned media (CM) and cell lysates (CL) of TM-5 cells expressing WT or mutant MYOC; FIG. 7B shows the MYOC accumulation and the presence of aggregates (shown by arrow); and FIG. 7C is a Western blot that shows the induction of apoptotic markers in mutant MYOC expressing cells.

FIGS. 9A and 9B show IOP levels were measured in 3 months old littermates of: FIG. 9A is a Wt mice, Tg-MYOCY$^{437H}$ mice, CHOP –/– mice & double mutant mice (Tg-MYOCY$^{437H}$/CHOP–/–); FIG. 9B shows the effect of 0.1% topical ocular dex treated WT mice, Vehicle treated WT mice (0.1% EtOH), Dex treated CHOP–/– mice & Vehicle treated CHOP–/– mice.

FIG. 10A is a Western blot showing myocilin and ER stress markers in TM-5 cells stably expressing mutant MYOC were transiently transfected with plasmids expressing Cas9-CHOP or ATF4; and FIG. 10B shows the CRISPR-CAS9 mediated deletion of CHOP verified in CRISPR-CHOP transfected clones by surveyor nuclear digestion analysis.

FIG. 11A is a Western blot of TM5 cells stably expressing mutant myocilin transfected with plasmid expressing CAS9-CHOP. Myocilin levels, autophagy marker (LC3B) and ER stress markers were analyzed; and FIG. 11B shows immunostaining showing Myocilin (Red), LC3B(Green) in TM5 cells stably expressing mutant myocilin transfected with plasmid expressing CAS9-CHOP.

FIG. 12A shows a Western blot of MYOC, ATF4 and CHOP in TM cells expressing WT or mutant MYOC treated with vehicle or ISRIB for 48 hours. FIG. 12B is a graph that shows the IOP of the left eyes of Tg-MYOC$^{Y437H}$ mice injected with ISRIB are compared with vehicle-injected contralateral right eyes. N=5; paired t-test.

FIG. 13A shows WT and Tg-MYOC$^{Y437H}$ mice were given topical eye drops of TS (left eyes) and TB (D11) in the contralateral right eyes for 2 weeks. IOP were measured weekly in the night. TB treatment reduced elevated IOP in Tg-MYOC$^{Y437H}$ mice but did not alter IOP in WT mice (n=6 each; one way ANOVA, *p<0.5). FIG. 13B shows IOP of the left eyes of Tg-MYOC$^{Y437H}$ mice given Torin-2 eye drops topically for 1 week compared with vehicle eye drops given to the contralateral right eyes. N=8; P<0.001, paired t-test.

DETAILED DESCRIPTION OF THE INVENTION

Figure 1B:
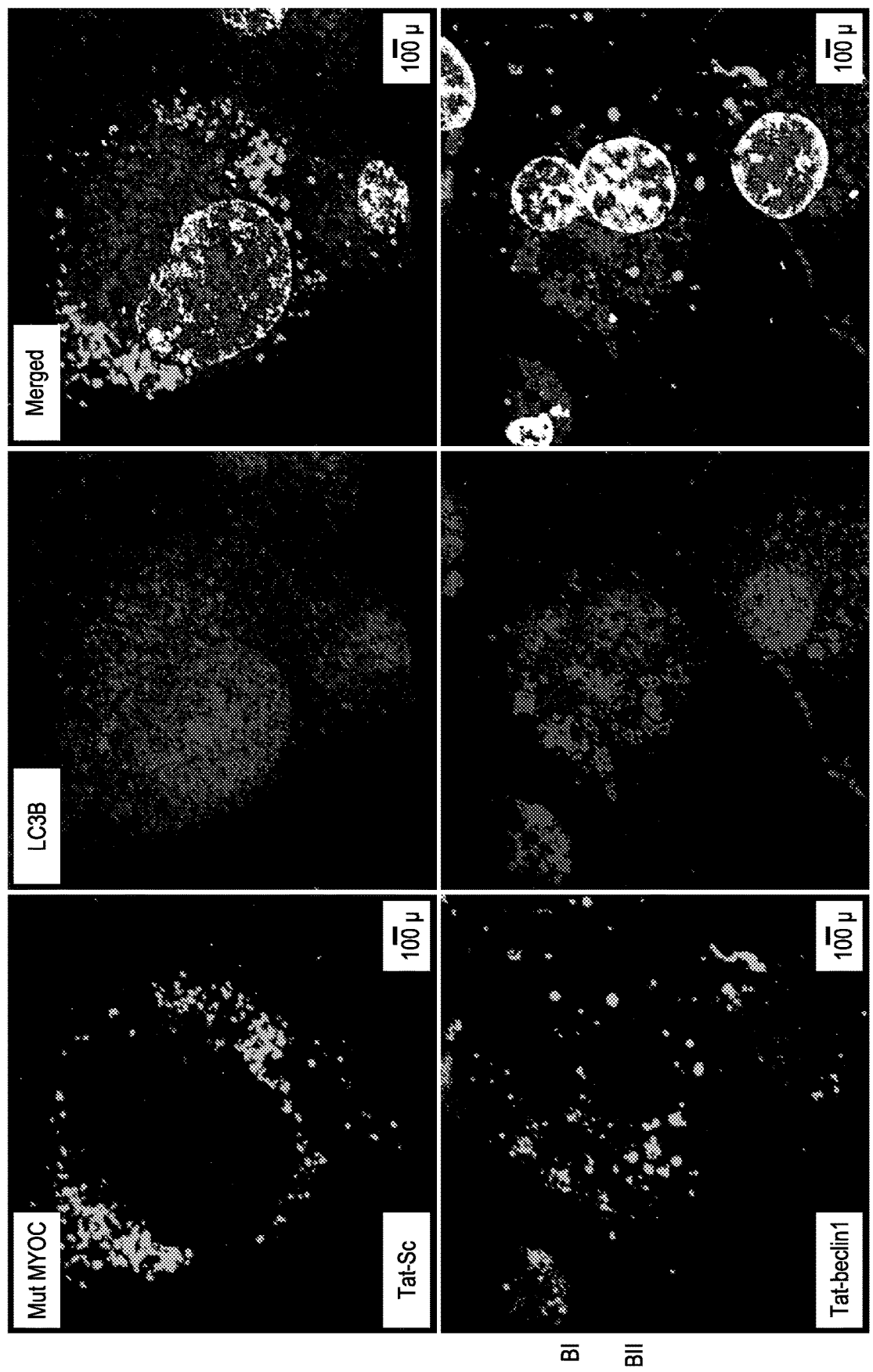
FIG. 1B shows the co-localization of LC3B positive autophagic vesicles (green) with MYOC (red) upon TB treatment.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. The present invention includes the treatment of glaucoma (and other ocular diseases) by enhancing or stimulating autophagy or correcting autophagy deficiency. Specifically, in addition to glaucoma the present invention can be used for the treatment of other ocular diseases associated with, e.g., Endoplasmic Reticulum (ER) stress and/or autophagy deficiency, Age-related Macular Degeneration (AMD), and/or Diabetic Retinopathy.

The present invention also includes compositions and methods for gene therapy modulation (inhibition) of ATF4 and/or CHOP to enhance autophagy for treatment of glaucoma/ocular diseases, including but not limited to, programmable gene editing nuclease (e.g., CRISPR-Cas) knockdown of ATF4 and/or CHOP, and/or other gene editing/ therapy techniques to reduce expression of ATF4 and/or CHOP (including but not limited to siRNA, miRNA).

The present invention also includes methods for using, and compositions that include proteins/peptides (Beclin 1, Tat-Beclin, Tat-Beclin D11), or small molecules for use in making a medicament for treating, and methods of treating ocular diseases by enhancing autophagy to treat the glaucoma and other ocular diseases caused by decreased autophagy.

The present invention also includes methods and compositions that include one or more chemical enhancers of autophagy for treatment of glaucoma/ocular diseases (use of Trehalose, Rapamycin, Torin-2). The present invention also includes methods and compositions that include one or more mTOR inhibitors that induce autophagy, including but not limited to Rapamycin, Torin-2, everolimus, temsirolimus, KU-0063794, WYE-354, AZD8055, metformin and derivatives, analogs or prodrugs thereof. Finally, the present invention also includes methods and compositions that use small molecule inhibitors of ATF4/CHOP pathway for treatment of glaucoma/ocular diseases (e.g., ISRIB).

A dosage unit for use of the composition of the present invention, may be a single compound or mixtures thereof with other compounds. In one non-limiting example, the composition may be a single dosed ampule or equivalent, or a dropper-bottle that includes the composition and can be provided to the subject in the form of drops. The compounds may be mixed together, may form ionic bonds, or covalent bonds. The composition of the present invention may be administered in cutaneous, subcutaneous, intraocular, or ocular form, all using dosage forms well known to those of ordinary skill in the pharmaceutical arts. Depending on the particular location or method of drops, serums, elixirs, tinctures, suspensions, syrups, and emulsions may be used to provide the composition of the present invention to a patient in need of therapy for a medical condition or symptom. The composition may also be administered as any one of known salt forms of the compounds or molecules used in the composition.

The composition of the present invention is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the composition may be formulated to provide, e.g., maximum and/or consistent dosing for the particular form for ocular administration. While the composition may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); Remington: The Science and Practice of Pharmacy, Pharmaceutical Press; 22nd Edition (2012), relevant portions incorporated herein by reference.

The present inventors recently linked protein misfolding and endoplasmic reticulum (ER) stress to the development of glaucomatous trabecular meshwork (TM) damage and intraocular pressure (IOP) elevation. TM cells activate protective unfolded protein response (UPR) pathway to eliminate abnormal protein accumulation. When the levels of unfolded proteins overwhelm ER-associated proteosomal degradation, cells have the capacity to activate autophagy, a compensatory lysosomal degradation system. Autophagy can adapt to cellular stress and act as a cell survival mechanism via clearance of misfolded proteins and reduction of abnormal protein accumulation. Defective autophagy can lead to accumulation of misfolded and abnormal proteins and cell death. The role of autophagy in regulation of IOP was investigated herein and treatments for IOP demonstrated. The results herein demonstrate for the first time that autophagy is impaired in the TM of mouse models of glaucoma as well as in human post-mortem glaucomatous TM tissues. Therefore, drugs that correct misfolding as well as enhance autophagic degradation of misfolded protein may reduce ER stress and prevent IOP elevation. The present inventors have found that treating trabecular meshwork pathology by drugs that reduce protein misfolding and increase abnormal misfolded protein degradation by autophagy significantly improve clinical outcomes and prevent irreversible blindness.

In the past, most efforts have been focused on using strategies to correct protein misfolding using drugs that enhance protein secretion. The present inventors have shown that sodium 4-phenylbutyrate enhances secretion of misfolded mutant myocilin, thus reducing ER stress and protects from ocular hypertension. In addition, other groups have shown that this approach reduces mutant myocilin accumulation in cell culture (*Invest Ophthalmol Vis Sci.* 2007 April; 48(4):1683-90). Until now, any role for autophagy in IOP elevation has not been explored. Cell culture studies suggest that knockdown of GRP94 reduces mutant myocilin and enhances autophagic clearance of mutant myocilin. The present invention shows for the first time that autophagy is impaired in glaucoma models and treating mice or cells with one or more specific stimulator of autophagy enhances autophagic degradation of mutant myocilin, reducing elevated IOP. Further, when combined with a chemical chaperone, a surprising synergistic effect is shown herein for the combination of an autophagy stimulator (enhancer or agonist) and a chemical protein chaperon. Other chemical chaperones for use with the present invention include, e.g., Histone deacetylase inhibitors (HDAC inhibitors). Non-limiting examples of HDAC selective and non-selective inhibitors include, but are not limited to: Vorinostat, Romidepsin, Chidamide, Panobinostat, Valproic acid (e.g., Mg valproate), Belinostat, Mocetinostat (MGCD0103), Abexinostat (PCI-24781), Entinostat (MS-275), SB939, Resminostat (4SC-201), Givinostat (ITF2357), Quisinostat, HBI-8000, Kevetrin, CUDC-101, AR-42, CHR-2845, CHR-3996, 4SC-202, CG200745, ACY-1215, lenalidomide, ME-344, and/or sulforaphane. Another chaperone protein includes Alpha-crystallin and members of the Alpha-crystallin (such as Alpha-crystallin EMBL: PF00525 or IPR003090) that act as protein chaperones.

Beclin1. In alternative embodiments, the invention provides for use of a sequence comprising all or a subsequence of Beclin1 or a peptidomimetic or synthetic form thereof, or an equivalent thereof, that induces, stimulates or increases autophagy.

One example of a Beclin1 amino acid sequence for use with the present invention is as follows: Length: 450 amino acids, Mass (Da): 51,896, Last modified: Feb. 21, 2001—v2: obtained from UniProtKB-Q14457-1 (BECN1_HUMAN).

```
            10         20         30         40
    MEGSKTSNNS TMQVSFVCQR CSQPLKLDTS FKILDRVTIQ 50         60         70         80
    ELTAPLLTTA QAKPGETQEE ETNSGEEPFI ETPRQDGVSR 90        100        110        120
    RFIPPARMMS TESANSFTLI GEASDGGTME NLSRRLKVTG 130        140        150        160
    DLFDIMSGQT DVDHPLCEEC TDTLLDQLDT QLNVTENECQ 170        180        190        200
    NYKRCLEILE QMNEDDSEQL QMELKELALE EERLIQELED 210        220        230        240
    VEKNRKIVAE NLEKVQAEAE RLDQEEAQYQ REYSEFKRQQ 250        260        270        280
    LELDDELKSV ENQMRYAQTQ LDKLKKTNVF NATFHIWHSG 290        300        310        320
    QFGTINNFRL GRLPSVPVEW NEINAAWGQT VLLLHALANK 330        340        350        360
    MGLKFQRYRL VPYGNHSYLE SLTDKSKELP LYCSGGLRFF 370        380        390        400
    WDNKFDHAMV AFLDCVQQFK EEVEKGETRF CLPYRMDVEK 410        420        430        440
    GKIEDTGGSG GSYSIKTQFN SEEQWTKALK FMLTNLKWGL

450
    AWVSSQFYNK
```

SEQ ID NO. 3, see www.uniprot.org/uniprot/Q14457#sequences.

Tat-beclin1 Peptide: Tat-beclin1 (TB) peptide was bought from EMD Millipore Corporation (MA, USA). TB was dissolved in sterile water and kept in −20° C. The peptide sequences for the Tat-beclin1 (TB) peptide is YGRK-KRRQRRR-GG-TNVFNATFEIWHDGEFGT (SEQ ID NO:1). Tat-beclin 1 is cell permeable and induces autophagy. Tat-scrambled Peptide: Tat-scrambled peptide (TS) was bought from AnaSpec, Inc. (CA, USA). TS was dissolved in sterile water and kept in −20° C. The Tat-Beclin-1, scrambled peptide sequences is YGRKKRRQR-RRGGVGNDFFINHETTGFATEW (SEQ ID NO:2), and does not induce autophagy and was used as a negative control as described previously (1). Furthermore, a shorter amino acid sequences for Tat-Beclin 1, D11, having an amino acid sequence: RRRQRRKKRGYGGDHWIHF-TANWV (SEQ ID NO:10), was also found to reduce IOP.

Treatment of trabecular meshwork (TM)-3 cells stably expressing DsRed tagged WT or Y437H mutant MYOC protein. The inventors recently generated TM-3 cells stably expressing DsRed tagged WT or Y437H mutant MYOC, which allows us to visualize myocilin in live cells and facilitates various therapeutic strategies. WT MYOC is secreted while mutant MYOC is not secreted and accumulates in the TM cells. Furthermore, mutant MYOC forms aggregates (B) and induces ER stress as described previously (2). TM-3 cells expressing mutant myocilin were grown on 24-well plate and incubated either with TS (control) or TB at various concentrations. 24 hours later, cell lysates were subjected for Western blot analysis of myocilin and ER stress as well as autophagy markers. Sodium 4-phenylbutyrate (PBA) was bought from Scandinavian Formulas, Inc. The PBA was dissolved in sterile water and cells were incubated at concentration of 1 mM. Trehalose was bought from Sigma. TM cells were incubated at concentration of 100 mM Rapamycin (bought from Sigma) of rapamycin for 24 hours.

Treatment of Tg-MYOC$^{Y437H}$ mice with Tat-beclin1 peptide: A detailed characterization of Tg-MYOC$^{Y437H}$ mice has been published previously (2). Tg-MYOC$^{Y437H}$ mice on C57BL/6J background were crossed with pure strain AJ mice and F1 mice were intercrossed. Age-matched WT and Tg-MYOC$^{Y437H}$ littermates were utilized for phenotype study and further biochemical analysis. Prior to treatment, IOP of WT and Tg-MYOC$^{Y437H}$ mice was measured to ensure IOP elevation in Tg-MYOC$^{Y437H}$ mice. The left eyes of WT or Tg-MYOC$^{Y437H}$ mice were given TB (5 mM) while the contralateral right eyes were given TS eye drops (5 mM) 3 times daily for 4 days. On fifth day, IOP were measured again.

Intraocular Pressure (IOP) Measurement.

Intraocular pressure (IOP) was determined in behaviorally trained conscious mice using a TonoLab rebound tonometer (Colonial Medical Supply), as described previously (3). Daytime IOP was measured between 9-11 am. The first three individual IOP measurements made were discarded; the following 10 individual IOP measurements were recorded. The mean±S.E.M. of the recorded readings was then calculated as the final IOP value for each eye at each IOP measurement.

1. Tat-beclin 1 peptide induces autophagic degradation of mutant myocilin in TM-5 cells and topical ocular Tat-beclin1 reduces elevated IOP in Tg-MYOC$^{Y437H}$ mice. The inventors determined whether improving autophagic flux via Tat-beclin (TB) 1 peptide reduces mutant MYOC. TM-5 cells stably expressing mutant MYOC were incubated with various doses of Tat-beclin 1 (TB) or Tat-scrambled (TS) peptide (FIG. 1A). Starting at 20 uM, TB reduced mutant MYOC and also increased LC3B II form as well as reduced p62 levels. Increased LC3B II form and reduced p62 levels indicate that TB activates autophagy and also reduces accumulation of misfolded proteins. Immunostaining for LC3B revealed induction of autophagy and co-localization myocilin within autophagic vesicles upon TB treatment (FIG. 1B). Co-localization of myocilin with LC3B further suggests active autophagic degradation of mutant myocilin when treated with TB while TS treated cells did not exhibit autophagy. Next, the inventors treated ocular hypertensive Tg-MYOC$^{Y437H}$ mice with topical TB or TS eye drops (FIG. 1C). The left eye was treated with TB and the contralateral right eye was given TS peptide twice daily for 4 days. Topical ocular TB significantly reduced elevated IOP compared to control contralateral eye treated with TS. TB treatment did not cause any toxicity or inflammation to the eyes.

Figure 2A:
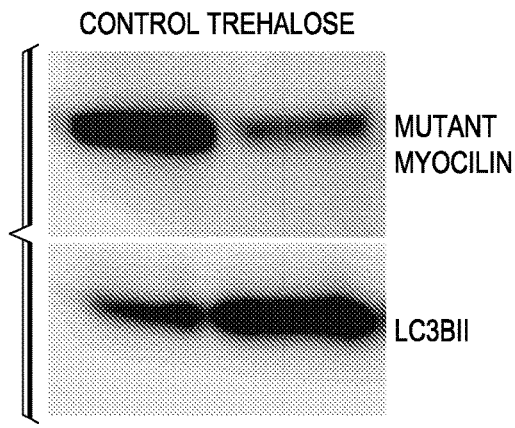
FIG. 2A shows the results from treating TM-3 cells expressing mutant myocilin with or without trehalose (100 mM) for 24 hours and cell lysates were subjected to Western blot analysis for myocilin and LC3B.
Figure 2B:
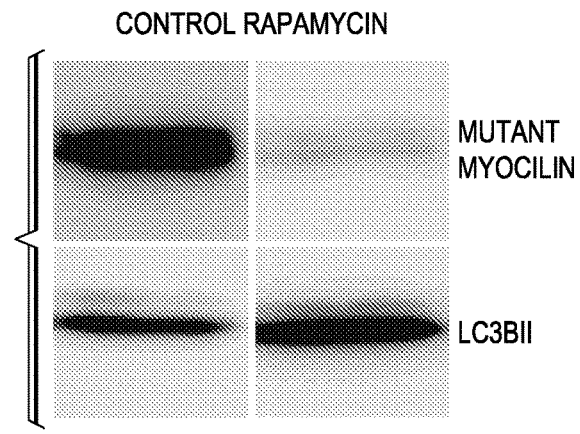
FIG. 2B shows the results from treating TM-3 cells expressing mutant myocilin with or without rapamycin for 24 hours and cell lysates were subjected to Western blot analysis for myocilin and LC3B. Both trehalose and rapamycin reduced mutant myocilin and also increased LC3BII, a marker of stimulated autophagy.
Figure 3:
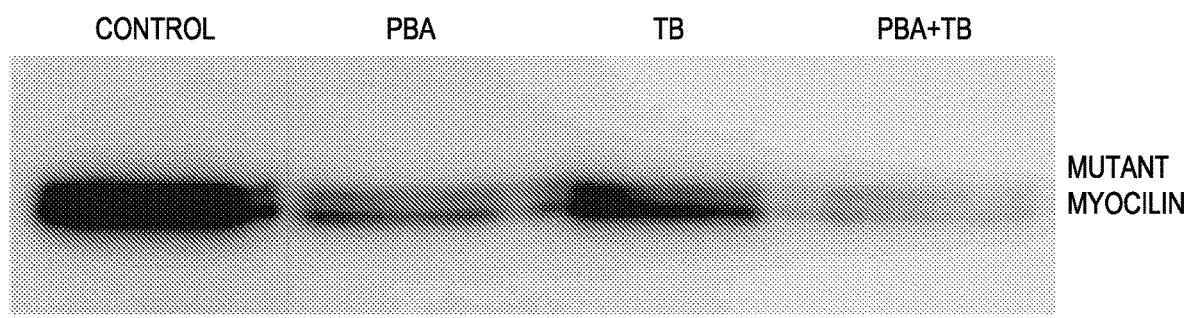
FIG. 3 shows the results from treating TM-3 cells expressing mutant myocilin with PBA (1 mM), TB or TB+PBA for 24 hours and cell lysates were subjected to Western blot analysis for MYOC.

2. General autophagy enhancers reduce mutant myocilin accumulation in TM cells. To test the inventors' findings that stimulation of autophagy reduces mutant myocilin accumulation in TM cells, the inventors tested the autophagy enhancers: Trehalose and rapamycin, on TM cells expressing mutant myocilin. Several studies have shown that trehalose and rapamycin stimulates autophagy and reduce misfolded proteins (4-6). Western blot analysis for myocilin accumulation revealed that treatment with trehalose (FIG. 2A) or rapamycin (FIG. 2B) reduces mutant myocilin dramatically and also induced autophagy as evident from increased LC3BII form. These studies demonstrate that stimulation of autophagy via known autophagy enhancers reduce mutant myocilin and further suggest that these autophagy enhancers can reduce elevated IOP in glaucoma. FIG. 2A shows the results from treating TM-3 cells expressing mutant myocilin with or without trehalose (100 mM) for 24 hours and cell lysates were subjected to Western blot analysis for myocilin and LC3B. FIG. 2B shows the results from treating TM-3 cells expressing mutant myocilin with or without rapamycin for 24 hours and cell lysates were subjected to Western blot analysis for myocilin and LC3B. Both trehalose and rapamycin reduced mutant myocilin and also increased LC3B-II, a marker of stimulated autophagy. FIG. 3 shows the results from treating TM-3 cells expressing mutant myocilin with PBA (1 mM), TB or TB+PBA for 24 hours and cell lysates were subjected to Western blot analysis for MYOC.

3. Combination of Tat-beclin and PBA synergistically reduces mutant myocilin accumulation in TM cells. The inventors have previously demonstrated that chemical chaperone; PBA reduces mutant myocilin and prevents glaucoma. The inventors demonstrated that PBA reduces elevated IOP via enhancing myocilin secretion and reducing endoplasmic reticulum stress in TM (2, 7). These data show that stimulation of autophagic degradation of mutant myocilin reduces elevated IOP. Therefore, it is possible that combination therapy of PBA to enhance secretion of mutant myocilin and autophagy stimulators to reduce mutant myocilin degradation will act synergistically to reduce protein misfolding and reduce elevated IOP more effectively. To test this hypothesis, the inventors treated TM cells expressing mutant myocilin with PBA alone, TB alone or combination of PBA with TB and examined mutant myocilin. Result show that PBA or TB alone reduces mutant myocilin. However, combination of PBA and TB reduce mutant myocilin more effectively than TB or PBA alone. These data demonstrate that a combination therapy of PBA and TB may reduce elevated IOP synergistically. Other chemical chaperones for use with the present invention include Histone deacetylase inhibitors (HDAC inhibitors) or an alpha-crystallin protein.

4. CRISPR for Glaucoma Treatment. Generation of plasmid expressing CRISPR-Cas9 targeting CHOP or ATF4. The human codon-optimized Cas9 plasmid pX459 (Addgene #48139) was obtained from Addgene (10). sgRNAs were designed and constructed as described previously (10,11). Briefly, target 20 bp sequences starting with guanine and preceding the PAM motif (5'-NGG-3') were selected from mouse Chop exon 2 and human ATF4 exon 2. (10,12). Potential off-target effects of sgRNA candidates were analyzed using the online tool CRISPR Design developed by Zhang's laboratory (http://crispr.mit.edu/).

One sgRNA in exon 2 of the mouse Chop gene (GACCACTCTGTTTCCGTTTCC) (SEQ ID NO:4) and exon 2 of the human ATF4 gene (AGGTCTCTTAGATGATTACC) (SEQ ID NO:5) was selected for transfection to create knockout cell lines. Clonal genomic DNA was extracted and used for PCR and Sanger sequencing. Primers for sequencing Chop were Chop-seqF (CACCACTCTTGACCCTGCTT) (SEQ ID NO:6) and Chop-seqR (GGGATTGAGGGTCACATCAT) (SEQ ID NO:7) and for ATF4 were ATF4-seqF (AACCGACAAAGACACCTTCG) (SEQ ID NO:8) and ATF4-seqR (ACCCTAGATCCCACCAGGAC) (SEQ ID NO:9).

Cell culture and Transfection. Human trabecular meshwork cells (TM-3) stably expressing human mutant myocilin were cultured in DMEM/F12 (Life Technologies) supplemented with 10% FCS. Cells were seeded in a 6-well plate at $1\times10^6$ cells/well. Transfection was performed with Lipofectamine 3000 using recommended conditions. Briefly, 2 ug of plasmid containing a sgRNA targeting either Chop exon 2 or ATF4 exon 2 and 6 ul Lipofectamine 2000 were diluted in 100 ul Opti-MEM, mixed 1:1 and added to cells after 5 minute incubation. After 24 hours, TM cell lysate was utilized for Western blotting. Western blot analysis and immunostaining for myocilin and other ER stress markers was performed as described previously (8,9).

CRISPR mediated CHOP/ATF4 knockdown induces autophagy mediated degradation of mutant myocilin. Elevation of intraocular pressure (IOP) is the major and only treatable risk factor in Primary Open Angle Glaucoma (POAG). The trabecular meshwork (TM) tissue in the eye regulates outflow resistance and maintains normal IOP. The glaucomatous TM damage is known to increase outflow resistance, thus elevating IOP. However, the lack of understanding of the pathological pathways that cause TM dysfunction has limited drug development targeted at the TM pathology. The inventors have demonstrated that chronic endoplasmic reticulum (ER) stress plays a key role in the glaucomatous TM damage & IOP elevation in MYOC-associated glaucoma (2), glucocorticoid (GC)-induced glaucoma (8) and also in human POAG cases (9). Abnormal protein accumulation in the TM is associated with induction of ER stress and IOP elevation in both of these mouse models.

TM cells activate the protective unfolded protein response (UPR) pathway to eliminate unfolded protein load by sensing through the ER stress sensors PERK, ATF6α, and IRE1, which then activate the downstream signaling to normalize ER homeostasis. Chronic and excessive ER stress can activate ATF4/CHOP signaling, which leads to apoptosis of TM cells and TM dysfunction. The inventors have also demonstrated that prodeath ER stress markers ATF4 and CHOP are significantly increased in the TM of human POAG patients (3). The inventors determined if inhibition of prodeath ATF4 and CHOP signaling prevents myocilin misfolding and TM dysfunction.

Figure 4:
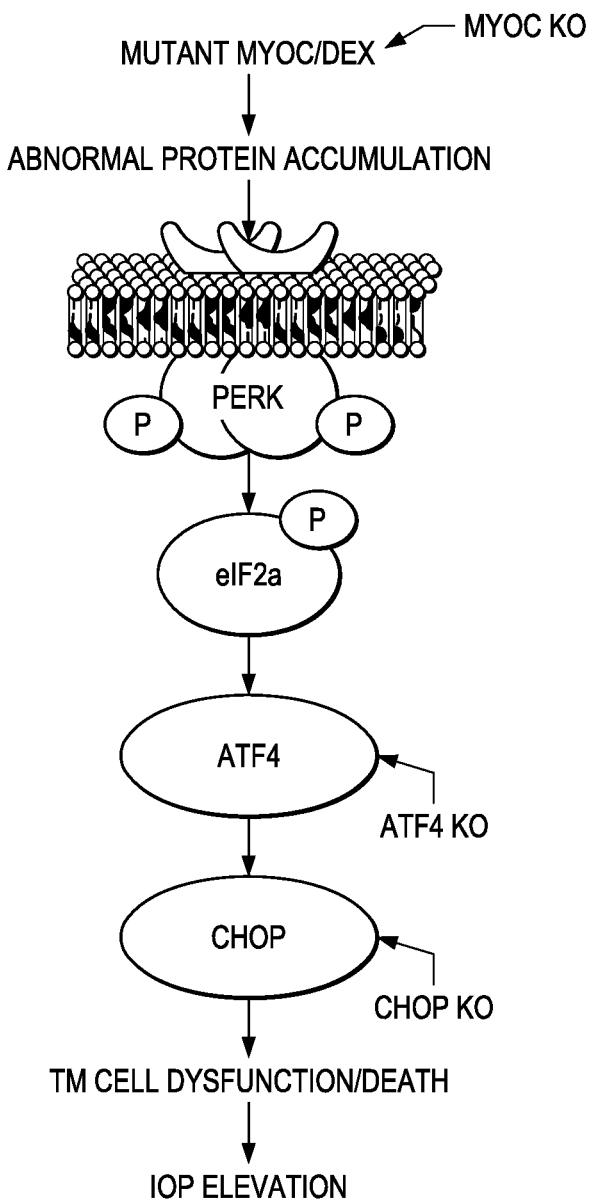
FIG. 4 is a drawing that shows the ATF4 and CHOP signaling pathway.

To inhibit ATF4/CHOP signaling, the inventors designed CRISPR-Cas9 targeting ATF4 or CHOP. FIG. 4 is a drawing that shows the ATF4 and CHOP signaling pathway.

IOP elevation and reduced outflow facility in mouse models of mutant myocilin induced glaucoma (Tg-Myoc$^{Y437H}$) and Dex induced glaucoma.

Figure 5A:
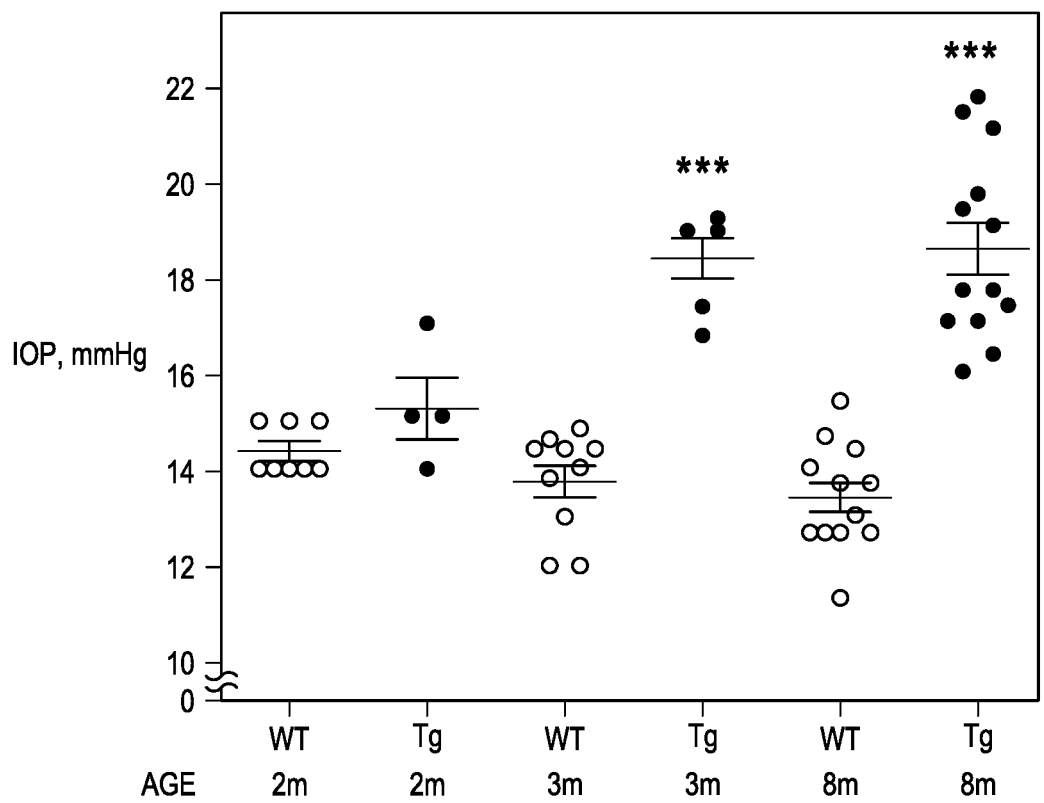
FIGS. 5A to 5D show.
Figure 5B:
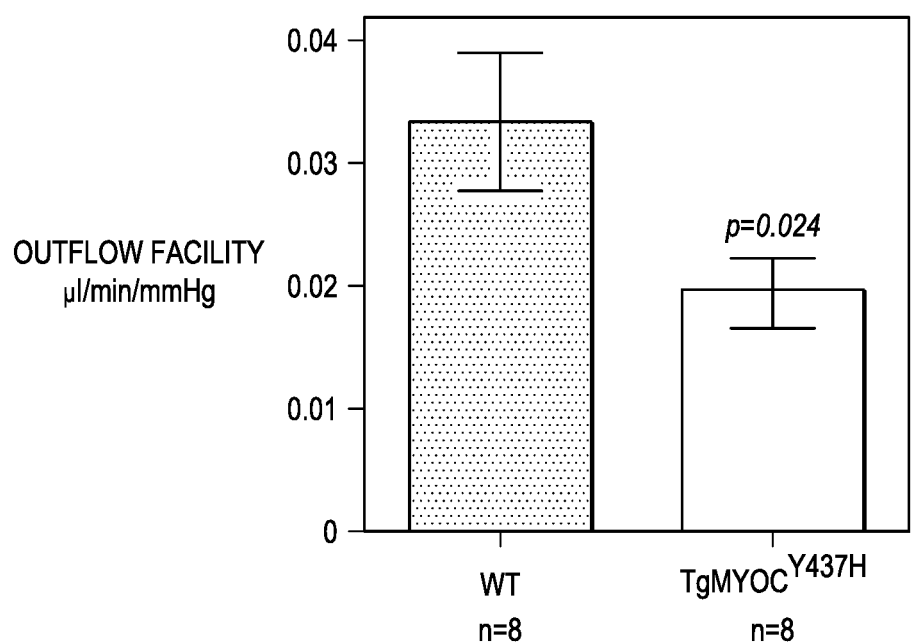
Figure 5C:
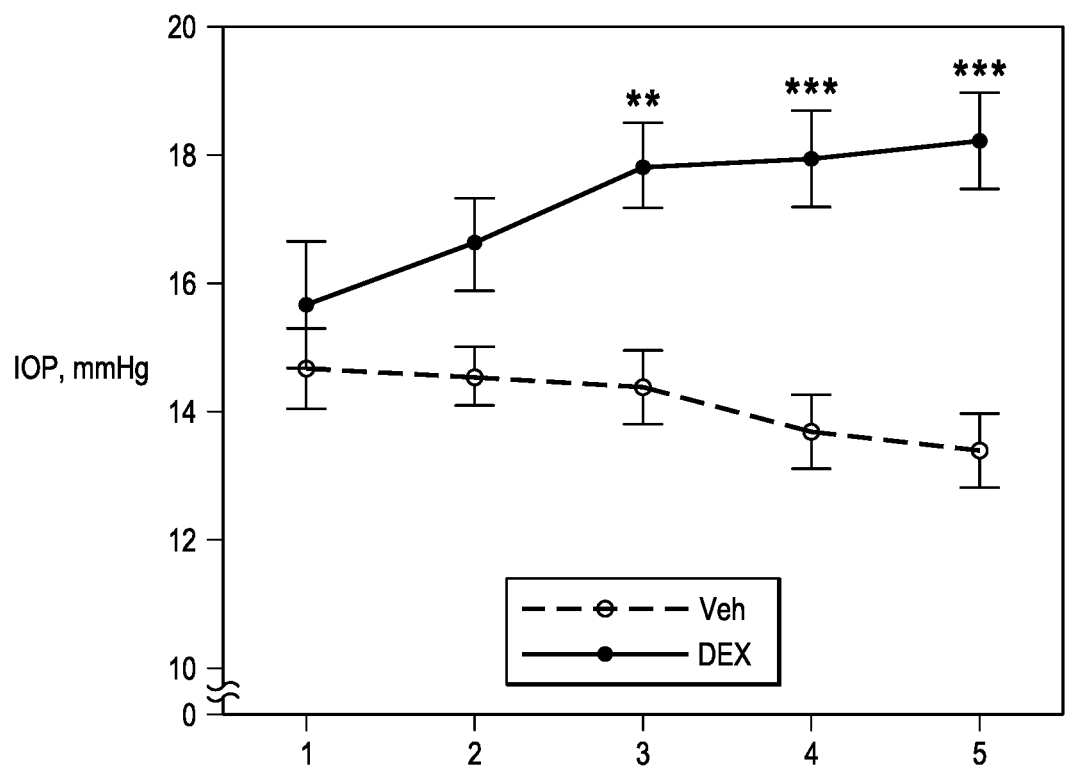
Figure 5D:
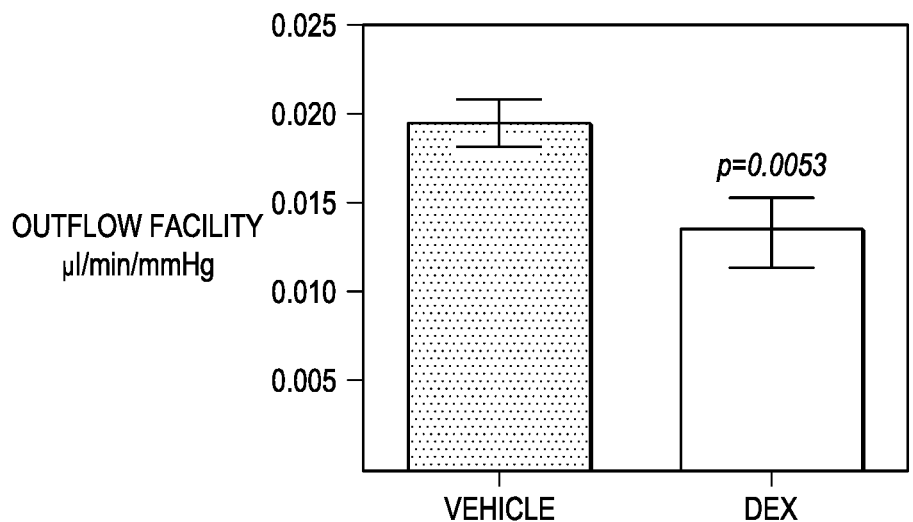

FIGS. 5A to 5D show as follows: FIG. 5A is a graph that shows IOP elevation in different aged group Tg-MYOC$^{Y437H}$ mice compared to wild-type (WT) litter mates (n=8); FIG. 5B is a graph that shows reduced outflow facility in 7 months old Tg-MYOC$^{Y437H}$ mice compared to WT littermates (n=8-10); FIG. 5C is a graph that shows IOP elevation in 0.1% topical ocular dex treated mice compared to vehicle treated mice; and FIG. 5D is a graph that shows reduced outflow facility in dex treated mice compared to vehicle treated mice (p<0.005, *p<0.0001; vs veh-treated mice; n=8).

Figure 6A:
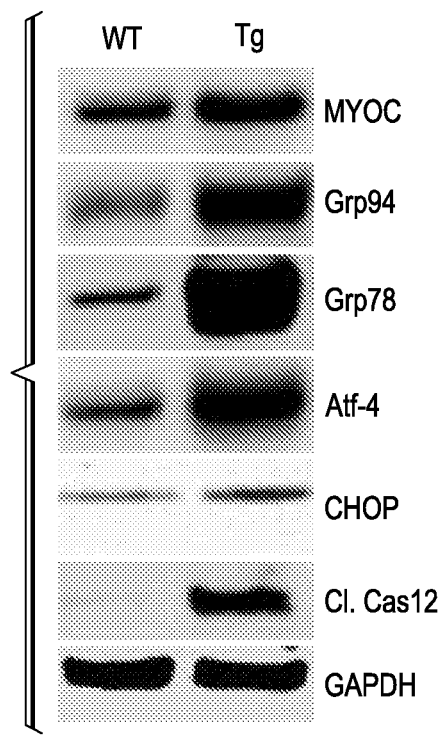
FIGS. 6A to 6C show Western blots of UPR markers, specifically.
Figure 6B:
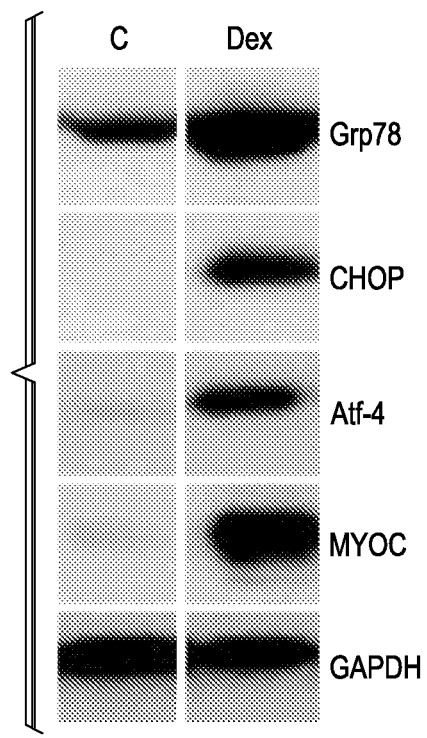
Figure 6C:
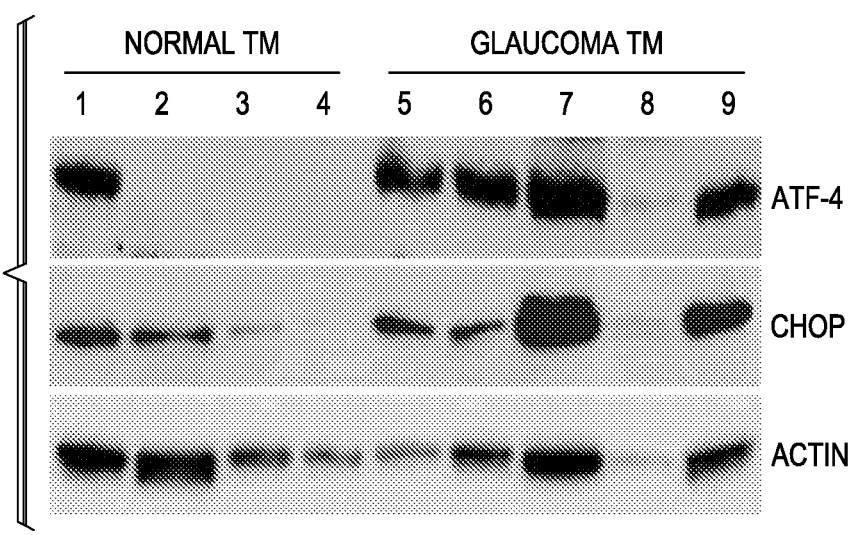
Figure 6D:
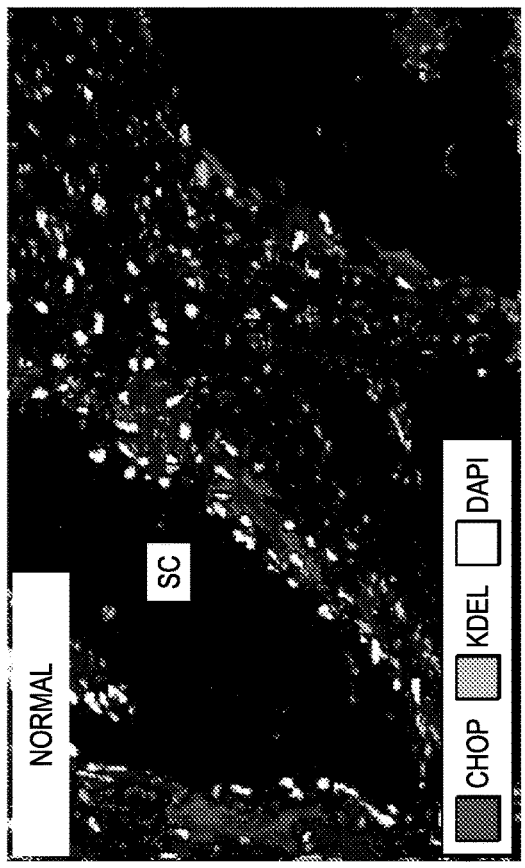
FIG. 6D shows immunostaining for CHOP & KDEL in normal and glaucomatous human TM tissues.
Figure 6D:
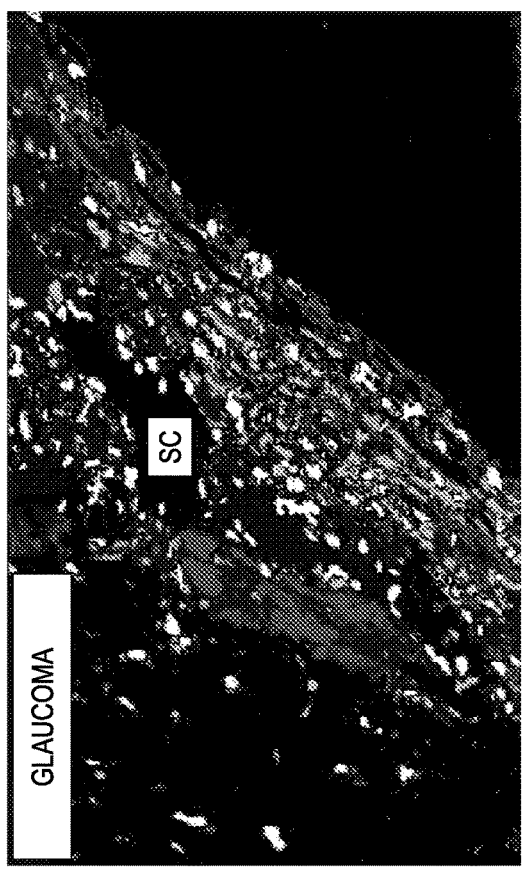

Induction of Prodeath ATF4 and CHOP in murine and human glaucoma. FIGS. 6A to 6C show Western blots of UPR markers, specifically: FIG. 6A is the anterior segment tissues of 6-month-old WT and Tg MYOC$^{Y437H}$ mice (n=3WT & 3 Tg); FIG. 6B is the anterior segment tissues of vehicle (n=4) and Dex (n=4)-treated mice; and FIG. 6C is a post-mortem human normal and glaucomatous TM tissues lysates (n=4). FIG. 6D show immunostaining for CHOP & KDEL in normal and glaucomatous human TM tissues.

Figure 7A:
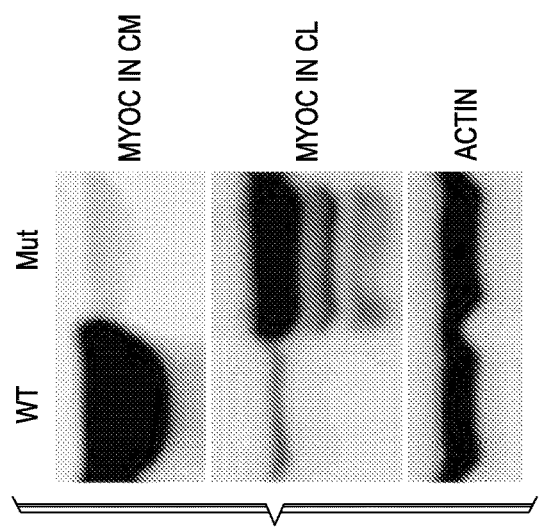
FIGS. 7A to 7C show.
Figure 7B:
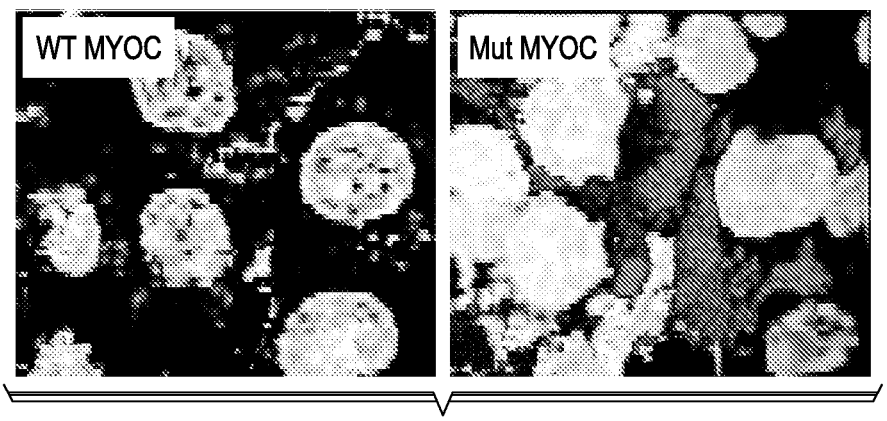
Figure 7C:
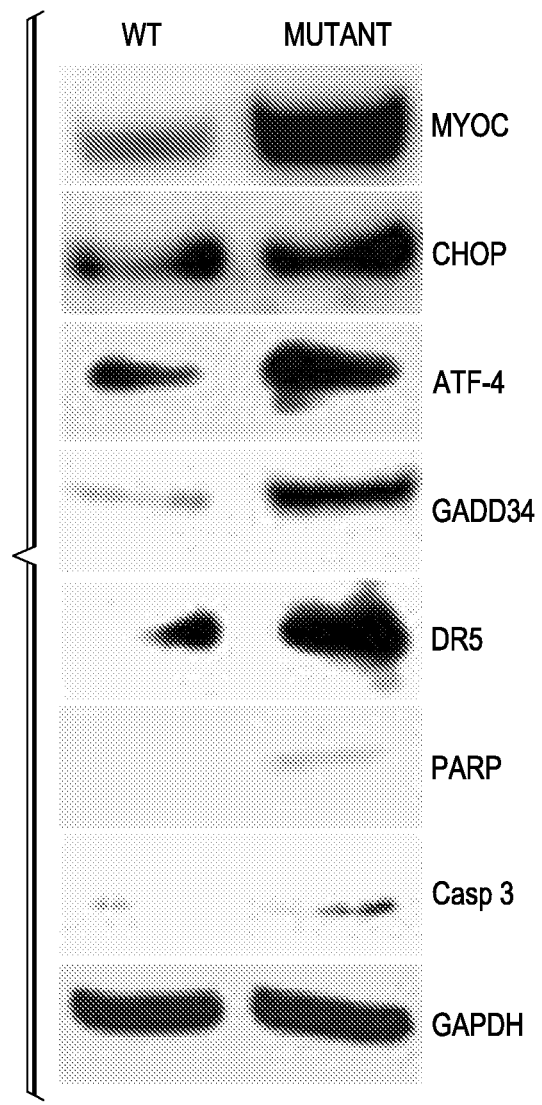

Induction of Apoptotic markers in TM cells expressing mutant Myocilin. FIGS. 7A to 7C show: FIG. 7A is a Western blot of MYOC in conditioned media (CM) and cell lysates (CL) of TM-5 cells expressing WT or mutant MYOC; FIG. 7B shows the MYOC accumulation and the presence of aggregates (shown by arrow); and FIG. 7C is a Western blot that shows the induction of apoptotic markers in mutant MYOC expressing cells.

Figure 8:
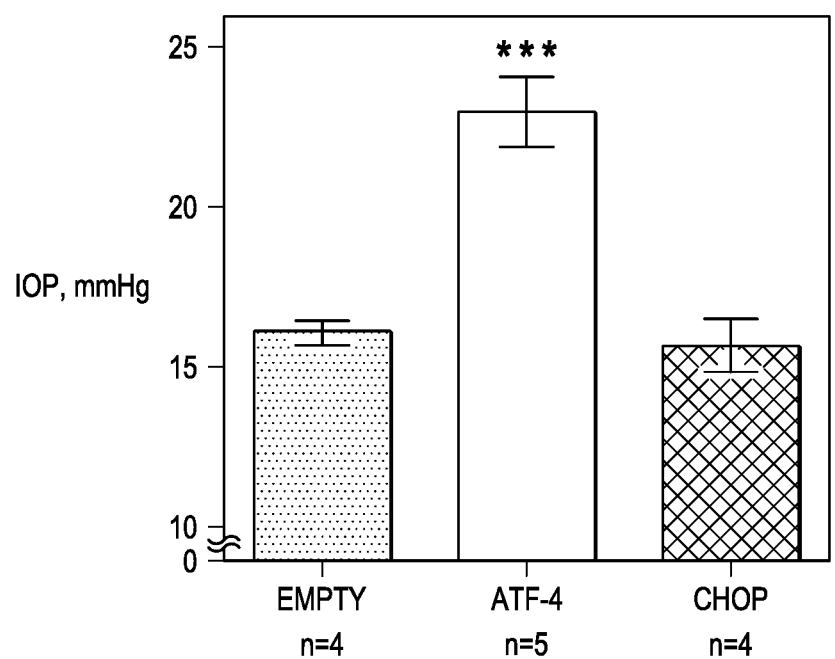
FIG. 8 shows IOP measured in WT mice intravitreally injected with 107 p.f.u. of Ad5 expressing null, ATF4 and CHOP (10-days post injections).

Overexpression of ATF4 in the TM elevates IOP in WT mice. FIG. 8 shows IOP measured in WT mice intravitreally injected with 10⁷ plu. of Ad5 expressing null, ATF4 and CHOP (10-days post injections).

Figure 9A:
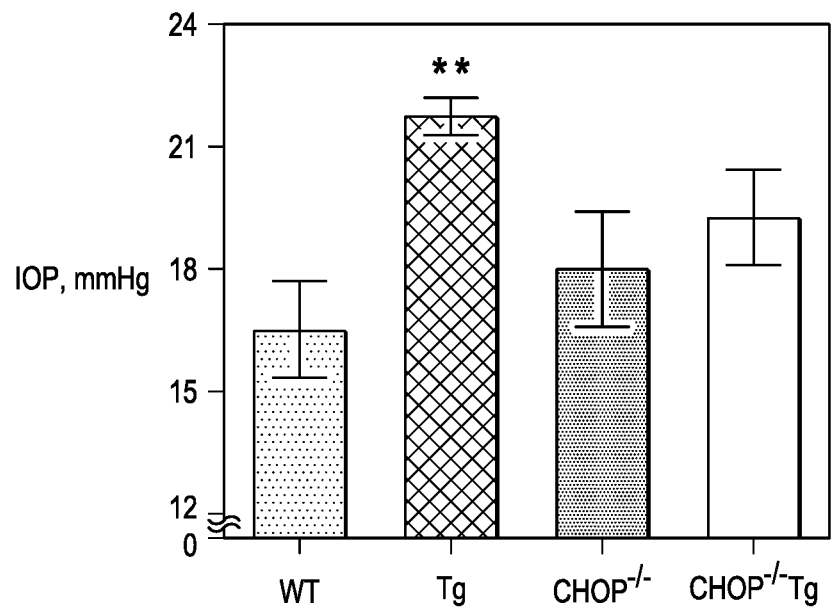
Figure 9B:
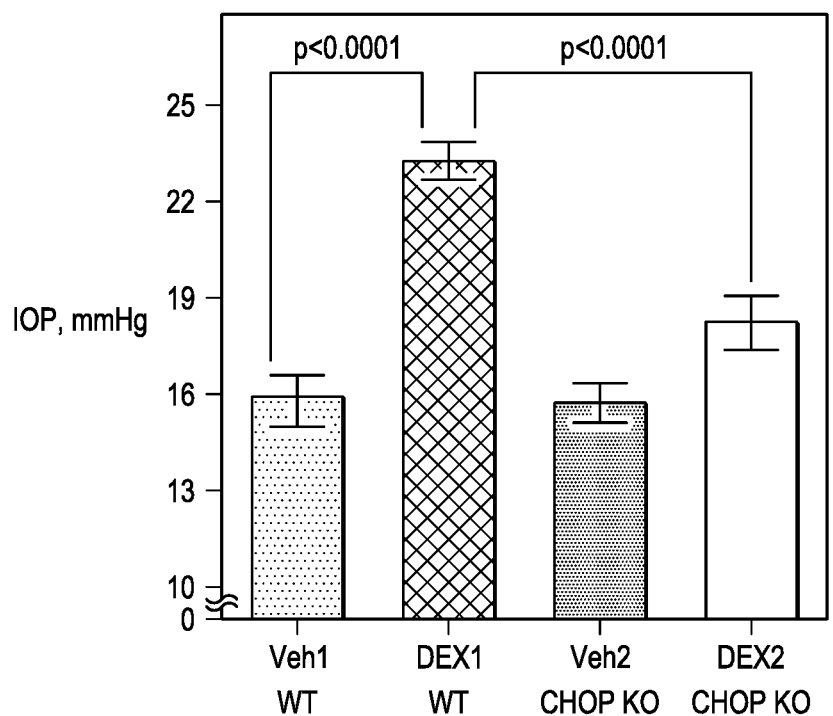

Deletion of CHOP rescues IOP elevation in mouse models of glaucoma. FIGS. 9A and 9B show IOP levels were measured in 3 months old littermates of: FIG. 9A is a Wt mice, Tg-MYOC$^{Y437H}$ mice, CHOP−/− mice and double mutant mice (Tg-MYOC$^{Y437H}$/CHOP−−/−); FIG. 9B shows the effect of 0.1% topical ocular dex treated WT mice, Vehicle treated WT mice (0.1% EtOH), Dex treated CHOP−/− mice and vehicle treated CHOP−/− mice.

Figure 10A:
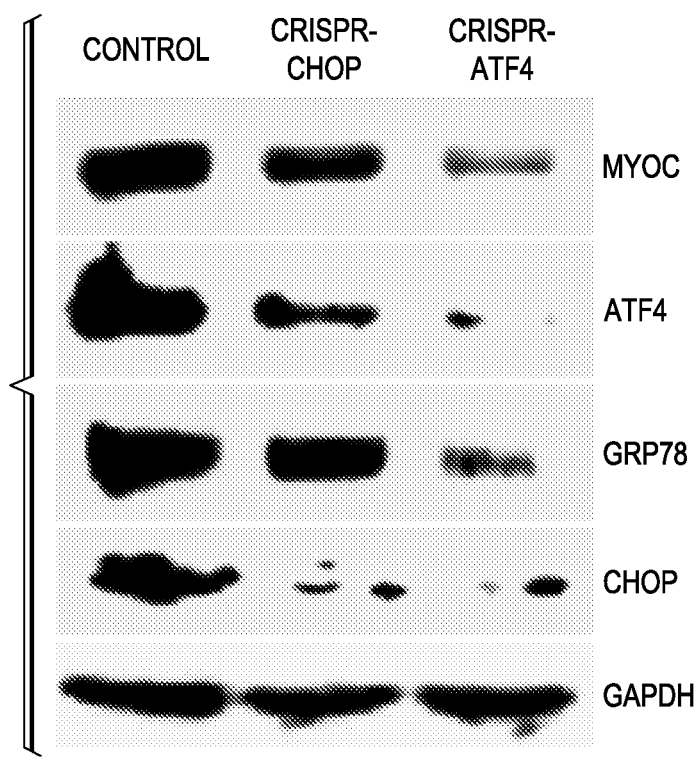
FIGS. 10A and 10B show.
Figure 10B:
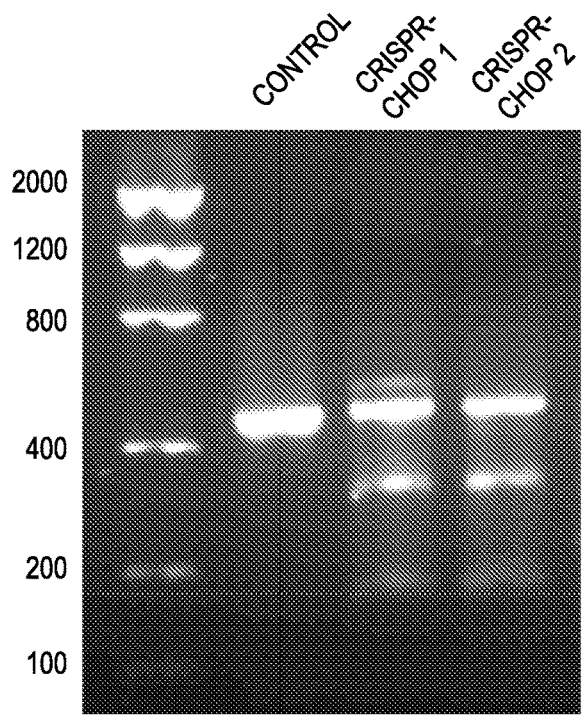

CRISPR-mediated ATF4 or CHOP deficiency reduces mutant myocilin accumulation in TM cells. FIGS. 10A and 10B show: FIG. 10A is a Western blot showing myocilin and ER stress markers in TM-5 cells stably expressing mutant MYOC were transiently transfected with plasmids expressing Cas9-CHOP or ATF4; and FIG. 10B shows the CRISPR-CAS9 mediated deletion of CHOP verified in CRISPR-CHOP transfected clones by surveyor nuclear digestion analysis.

Figure 11A:
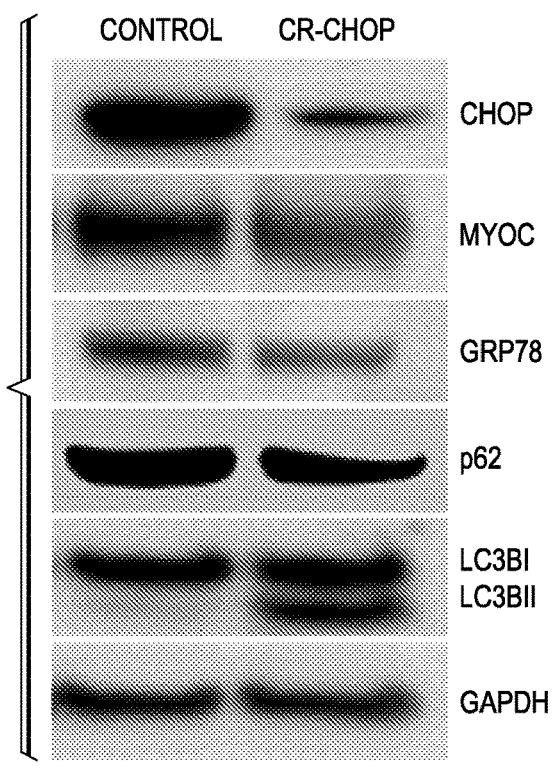
FIGS. 11A and 11B show as follows.
Figure 11B:
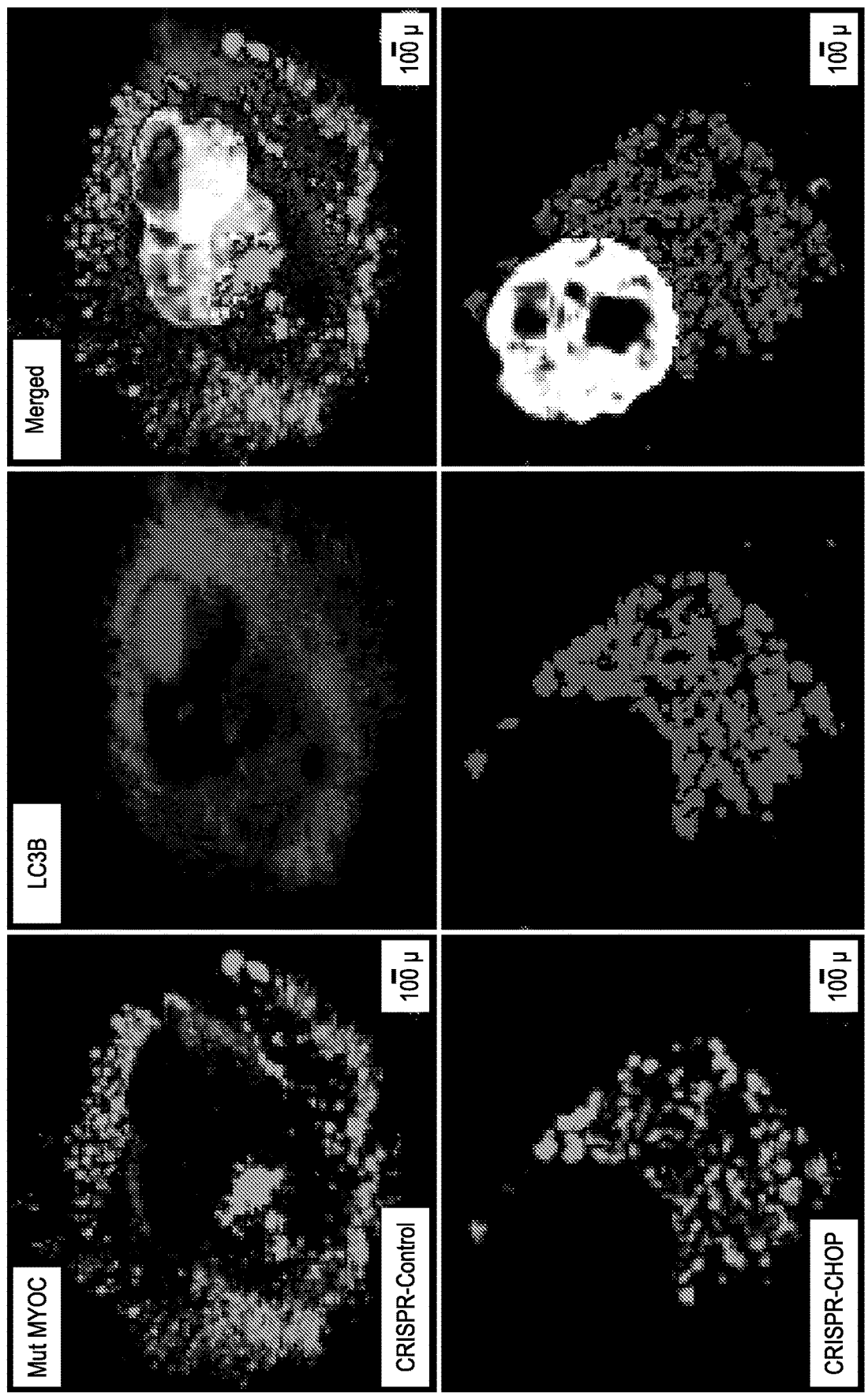

CRISPR mediated CHOP/ATF4 knockdown induces autophagy-mediated degradation of mutant myocilin. FIGS. 11A and 11B show: FIG. 11A is a Western blot of TM5 cells stably expressing mutant myocilin transfected with plasmid expressing CAS9-CHOP. Myocilin levels, autophagy marker (LC3B) and ER stress markers were analyzed; and FIG. 11B shows immunostaining showing Myocilin (Red), LC3B (Green) in TM5 cells stably expressing mutant myocilin transfected with plasmid expressing CAS9-CHOP.

Figure 12A:
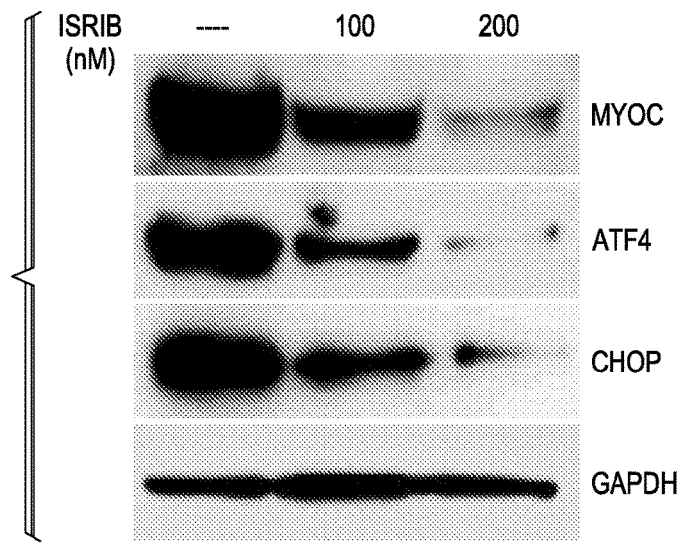
FIGS. 12A and 12B show the effect of ISRIB on mutant myocilin accumulation.
Figure 12B:
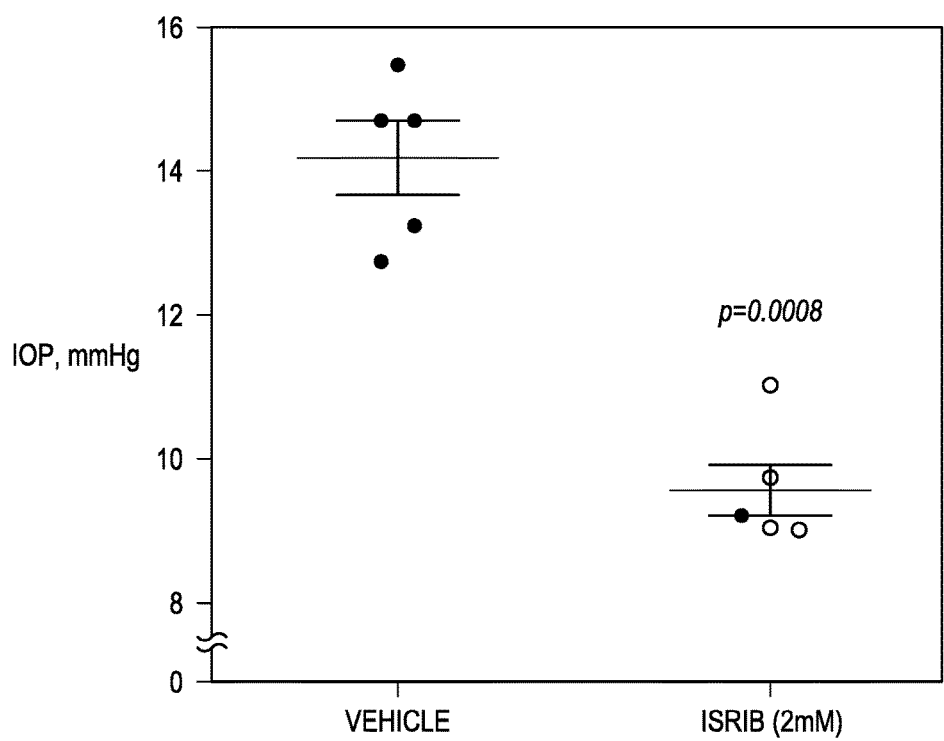

FIGS. 12A and 12B show that Integrated Stress Response Inhibitor (ISRIB or trans-N,N'-(cyclohexane-1,4-diyl)bis(2-(4-chlorophenoxy)acetamide), Chem Spider No. 30773985) prevents mutant myocilin accumulation in TM-5 cells and reduces elevated IOP in Tg-MYOC$^{Y437H}$ mice. The inventors examined whether ISRIB treatment reduces mutant myocilin accumulation in TM-5 cells stably expressing mutant myocilin. Compared to control TM-5, which shows accumulation of mutant myocilin, ISRIB (100 and 200 nM) treatment dramatically reduced myocilin accumulation. ISRIB also inhibited ATF4 and CHOP as evident from reduced cellular protein levels. Furthermore, the inventors performed an intravitreal injection of vehicle (right eye) or ISRIB (2 mM, 2 ul, left eye) in ocular hypertensive Tg-MYOC$^{Y437H}$ mice (4-months-old). IOP measurements after 1-week treatment revealed that ISRIB significantly reduced elevated IOP compared to the vehicle-treated contralateral eyes. In addition ISRIB treated mice did not show any signs of inflammation or other ocular toxicity in slit lamp analysis. FIG. 12A is a Western blot of MYOC, ATF4 and CHOP in TM cells expressing WT or mutant MYOC treated with vehicle or ISRIB for 48 hours. FIG. 12B is a graph that shows the IOP of the left eyes of Tg-MYOCY437H mice injected with ISRIB are compared with vehicle-injected contralateral right eyes. N=5; paired t-test.

Figure 13A:
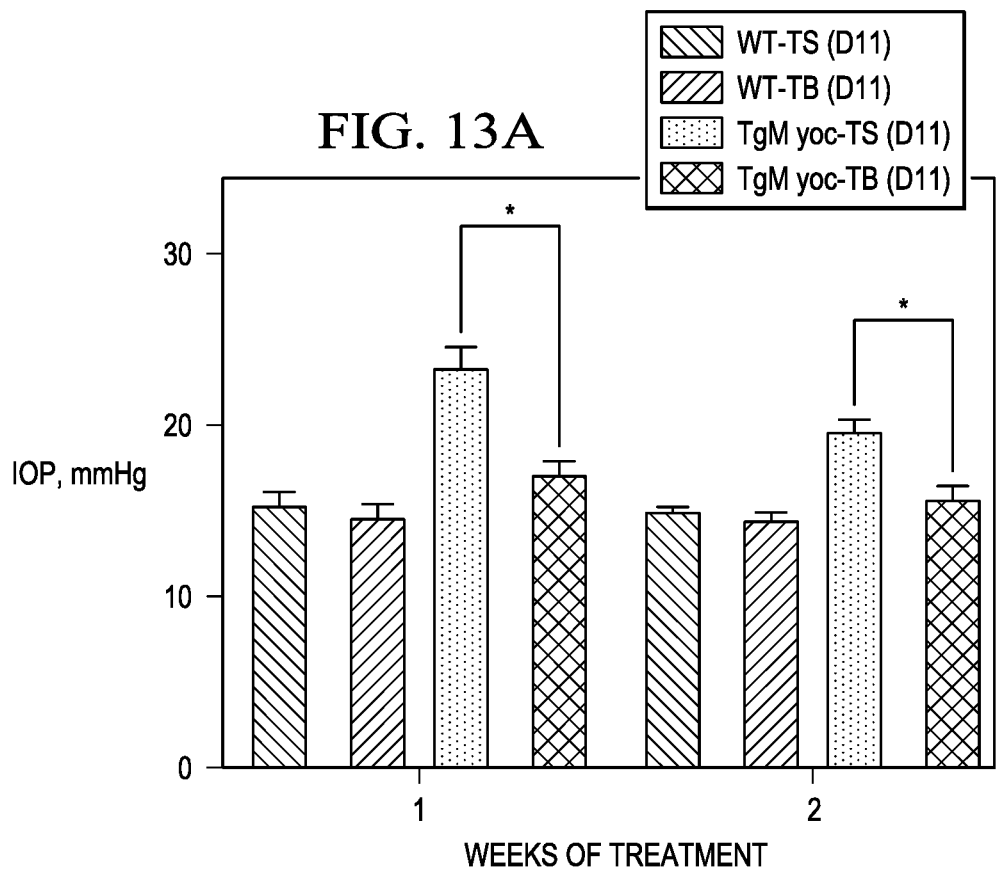
FIGS. 13A and 13B show the effects of autophagy stimulator Tat-Beclin 1 D11, a shorter Tat-Beclin 1 peptide, on IOP.

Next, the inventors treated ocular hypertensive Tg-MYOC$^{Y437H}$ mice with topical TB or TS eye drops (FIG. 13A). The left eye was treated with TB and the contralateral right eye was given TS peptide twice daily for 2 weeks. TB treatment did not alter IOP in WT mice. Topical ocular TB significantly reduced elevated IOP compared to control contralateral eye treated with TS. TB treatment did not cause any toxicity or inflammation to the eyes. Similar to TB treatments, the inventors also used another stimulator of autophagy, Torin-2 ((9-(6-Amino-3-pyridinyl)-1-[3-(trifluoromethyl)phenyl]-benzo[h]-1,6-naphthyridin-2(1H)-one)).

Figure 13B:
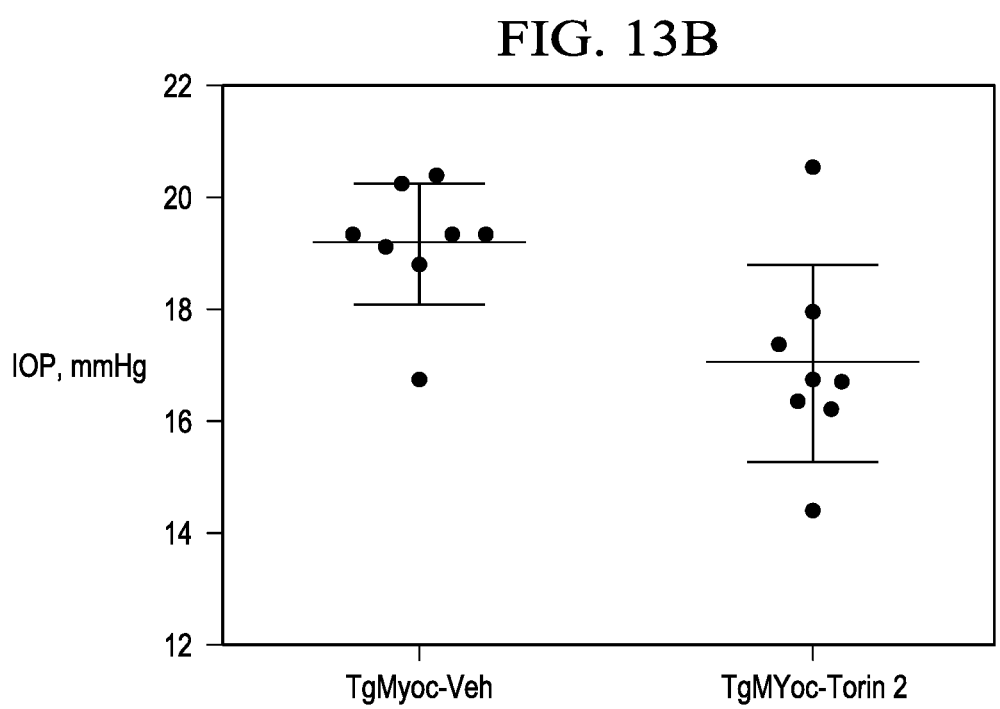

Torin-2 is a Mammalian target of rapamycin (mTOR) inhibitor. Treatment of ocular hypertensive Tg-MYOC$^{Y437H}$ mice with Torin-2 dramatically reduced IOP within 1 week of treatment compared to the contralateral vehicle treated eyes (FIG. 13B). FIG. 13A compares WT and Tg-MYOC$^{Y437H}$ mice were given topical eye drops of TS (left eyes) and TB (D11) in the contralateral right eyes for 2 weeks. IOP were measured weekly in the night. TB treatment reduced elevated IOP in Tg-MYOC$^{Y437H}$ mice but did not alter IOP in WT mice (n=6 each; one way ANOVA, *p<0.5). FIG. 13B shows is a graph that shows the IOP of the left eyes of Tg-MYOC$^{Y437H}$ mice given Torin-2 eye drops topically for 1 week compared with vehicle eye drops given to the contralateral right eyes. N=8; P<0.001, paired t-test. As such, the autophagy stimulators Tat-Beclin 1 D11 (shorter beclin peptide conjugated to Tat) and Torin-2 reduced elevated IOP in Tg mice.

Next, the inventors used CRISPR-Cas9 expressing guide RNA for ATF4 deletion rescues mouse model of glucocorticoid-induced glaucoma. The inventors have developed a mouse model of glucocorticoid-induced ocular hypertension. Weekly periocular injections of a potent glucocorticoid, dexamethasone acetate suspension (Dex) elevates IOP significantly starting from 1 week of treatment. To determine whether CRISPR-Cas9 targeted genetic deletion of ATF4 rescues mouse model of glucocorticoid-induced IOP elevation, C57 mice were injected with intravitreal injections of adenovirus expressing CRSPR-Cas9 ATF-4. One week after injections, mice were given periocular injections of Veh or Dex and IOP were monitored. IOP measurement revealed that control mice (without CR-ATF4) elevated IOP significantly while mice injected with CR-ATF4 did not elevate IOP significantly. These data demonstrate that targeting ATF4 knockdown via CRISPR-Cas9 rescues glucocorticoid-induced glaucoma.

Figure 14:
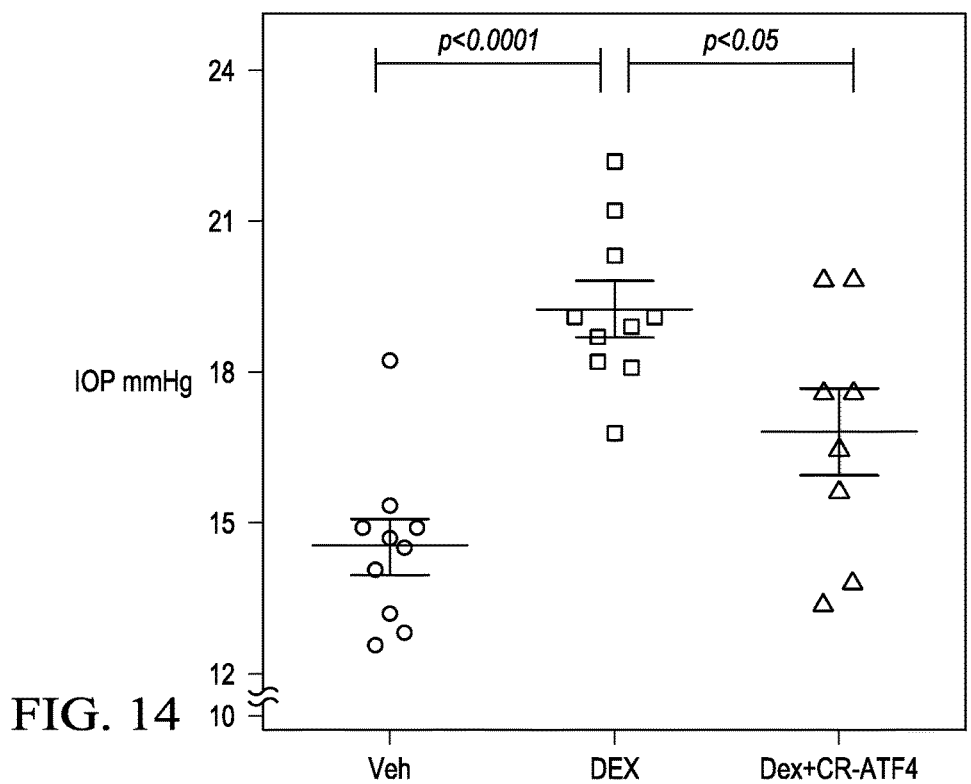
FIG. 14 is a graph that shows IOP measurements in mice treated with CR-ATF4.

FIG. 14 is a graph that shows IOP measurements in mice treated with CR-ATF4. C57 mice were injected with or without CR-ATF4. One week later, mice were treated with periocular injections of Veh or Dex and IOPs were monitored after 1 week. Compared to mice treated with Dex alone, mice treated with CR-ATF4 and Dex demonstrated significantly reduced IOP similar to vehicle treated mice.

Figure 15:
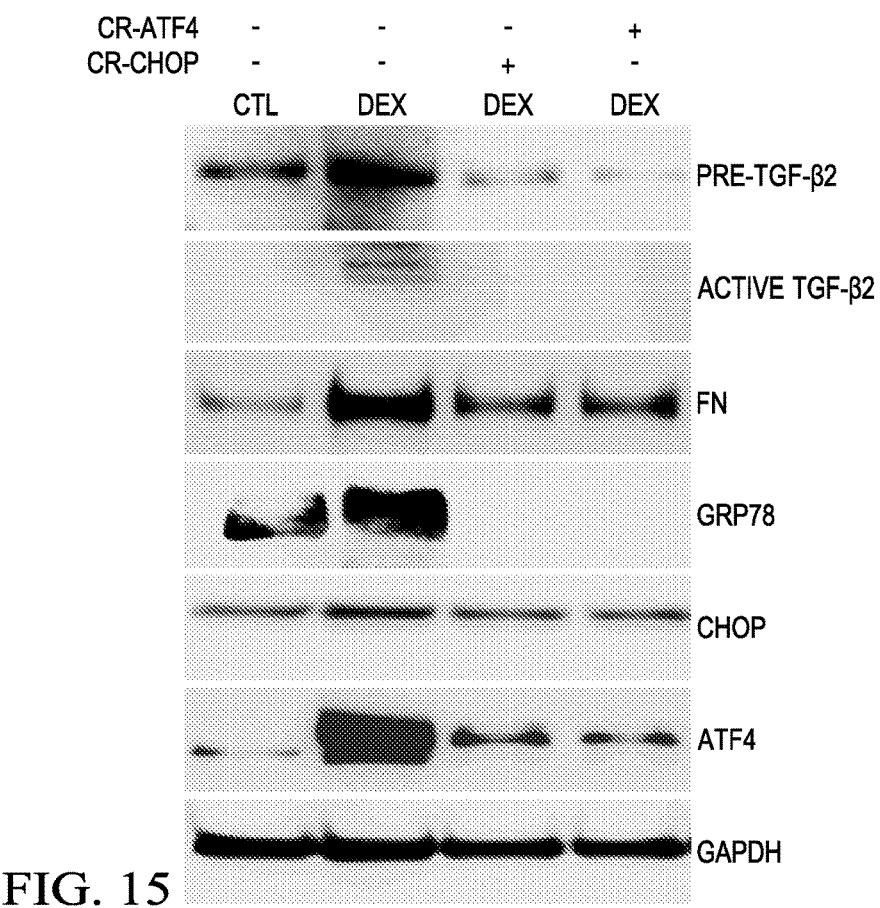
FIG. 15 shows that knockdown of ATF4 or CHOP inhibits TGFβ2 signaling and prevents abnormal Dex-induced ECM accumulation and ER stress in TM cells.

ATF4 and CHOP knockdown prevents activation of TGF-β2 signaling and also reduces intracellular ECM accumulation in the TM. The inventors have previously demonstrated that Dex induces expression of terminal ER stress markers such as ATF4 and CHOP. Moreover, CHOP knock out mice are protected from Dex-induced ocular hypertension. However, it is not clear how loss of CHOP protects from Dex-induced IOP elevation. Here, the inventors examined whether loss of ATF4 or CHOP inhibits TGFβ2 signaling, thus preventing abnormal ECM accumulation and induction of ER stress (FIG. 15). TM3 cells were transfected with CRISPR-Cas9 targeted to CHOP or ATF4 for 24 hours, and then treated with Veh or Dex for an additional 48 hours. Western blot analysis demonstrated that Dex increases precursor and active TGFβ2, fibronectin, and ER stress markers including GRP78, ATF4 and CHOP, which were reduced to normal levels in cells pretreated with CR-ATF4 or CR-CHOP. Western blot data further confirmed that CR-ATF4 or CR-CHOP treatment reduced protein levels of ATF4 and CHOP in TM cells transfected with these plasmids and treated with Dex. Furthermore, CHOP or ATF4 knockdown decreased Dex-induced expression of pro and active TGFβ2 levels (FIG. 15).

FIG. 15 shows that knockdown of ATF4 or CHOP inhibits TGFβ2 signaling and prevents abnormal Dex-induced ECM accumulation and ER stress in TM cells. TM3 cells transiently transfected with CRISPR-Cas9-CHOP or CRISPR-Cas9-ATF4 and treated with Veh or Dex for 48 hours. Cell lysates were analyzed for expression levels of fibronectin, TGFβ2 and ER stress markers by Western blotting.

It was found that chronic or sustained ER stress either in mutant myocilin or Dexamethasone induced glaucoma trigger induction of ATF4/CHOP, which is associated with TM cell dysfunction/death and IOP elevation. Inhibition of ATF4/CHOP pathway by genetic knockdown (CAS9 mediated knockdown of ATF4 or CHOP) allows pro-survival UPR mechanisms to cope up with protein misfolding, thus preventing TM cell death and IOP elevation.

It is contemplated that any embodiment discussed in this specification can be implemented with respect to any method, kit, reagent, or composition of the invention, and vice versa. Furthermore, compositions of the invention can be used to achieve methods of the invention. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Shoji-Kawata S, Sumpter R, Leveno M, Campbell G R, Zou Z, Kinch L, Wilkins A D, Sun Q, Pallauf K, MacDuff D, et al. Identification of a candidate therapeutic autophagy-inducing peptide. Nature. 2013; 494(7436): 201-6.
2. Zode G S, Kuehn M H, Nishimura D Y, Searby C C, Mohan K, Grozdanic S D, Bugge K, Anderson M G, Clark A F, Stone E M, et al. Reduction of ER stress via a chemical chaperone prevents disease phenotypes in a mouse model of primary open angle glaucoma. J Clin Invest. 2011; 121(9):3542-53.
3. Wang W H, Millar J C, Pang I H, Wax M B, and Clark A F. Noninvasive measurement of rodent intraocular pressure with a rebound tonometer. Invest Ophthalmol Vis Sci. 2005; 46(12):4617-21.
4. Sarkar S, Davies J E, Huang Z, Tunnacliffe A, and Rubinsztein D C. Trehalose, a novel mTOR-independent autophagy enhancer, accelerates the clearance of mutant huntingtin and alpha-synuclein. J Biol Chem. 2007; 282 (8):5641-52.
5. Sarkar S, Chigurupati S, Raymick J, Mann D, Bowyer J F, Schmitt T, Beger R D, Hanig J P, Schmued L C, and Paule M G. Neuroprotective effect of the chemical chaperone, trehalose in a chronic MPTP-induced Parkinson's disease mouse model. Neurotoxicology. 2014; 44(250-62.
6. Renna M, Jimenez-Sanchez M, Sarkar S, and Rubinsztein D C. Chemical inducers of autophagy that enhance the clearance of mutant proteins in neurodegenerative diseases. J Biol Chem. 2010; 285(15):11061-7.
7. Zode G S, Bugge K E, Mohan K, Grozdanic S D, Peters J C, Koehn D R, Anderson M G, Kardon R H, Stone E M, and Sheffield V C. Topical ocular sodium 4-phenylbutyrate rescues glaucoma in a myocilin mouse model of primary open-angle glaucoma. Invest Ophthalmol Vis Sci. 2012; 53(3):1557-65.
8. Zode G S et al. ER stress reduction rescues glaucoma in murine glucocorticoid-induced glaucoma. J Clin Invest. 2014; 124(5):1956-65.
9. Peters J C et al. Increased Endoplasmic Reticulum Stress in Human Glaucomatous Trabecular Meshwork Cells and Tissues. Invest Ophthalmol Vis Sci. 2015; 56(6):3860-8.

What is claimed is:

1. A composition for the treatment of an eye disease comprising a therapeutically effective amount of an inhibitor of a CHOP gene, an ATF4 gene, or both, comprising a gene knockdown construct selected from at least one of an siRNA, a miRNA, an shRNA, an antisense RNA, or an sgRNA, a programmable gene editing nuclease (CRISPR-Cas) knockdown of ATF4 and/or CHOP, or a gene editing or therapy that reduces expression of ATF4 and/or CHOP, wherein the construct targets an exon, intron, or exon/intron junction of a human CHOP gene and/or an exon, intron, or exon/intron junction of a human ATF4 gene.

2. The composition of claim 1, wherein the amount of the composition is sufficient to reduce at least one of protein misfolding, defective autophagy, or endoplasmic reticulum stress or increase autophagy.

3. The composition of claim 1, further comprising a synergistic amount of a protein chaperone sufficient to treat or slow the progression of the eye disease.

4. The composition of claim 1, wherein the eye disease comprises one or more symptoms selected from at least one of elevated intraocular pressure, increased aqueous humor outflow resistance at the trabecular meshwork, accumulation of misfolded proteins, or cell death.

5. The composition of claim 1, wherein the composition is adapted for subcutaneous, cutaneous, intravitreal, intraocular, or ocular administration.

6. The composition of claim 1, wherein the eye disease is caused by misfolded proteins, the loss of clearance of misfolded proteins, the accumulation of misfolded proteins, or a decrease in lysosomal activity.

7. The composition of claim 1, wherein the eye disease is glaucoma, endoplasmic reticulum (ER) stress, autophagy deficiency, age-related macular degeneration (AMD), or diabetic retinopathy.

8. The composition of claim 1, wherein the composition further comprises one or more pharmaceutically acceptable excipients.

9. The composition of claim 1, wherein the sgRNA construct comprises at least one of (GACCACTCTGTTTC-CGTTTCC) (SEQ ID NO:4) or (AGGTCTCTTAGATGAT-TACC) (SEQ ID NO:5).

10. The composition of claim 1, further comprising a protein chaperone selected from 4-phenylbutyrate or a salt thereof, 1-deoxygalactonojirimycin or a salt thereof, isofagomine or a salt thereof, fagomine isomers or a salt thereof, dimethylsulfoxide (DMSO) or a salt thereof, tauroursodeoxycholic acid (TUDCA) or a salt thereof, ursodeoxycholic acid (UDCA) or a salt thereof, glycine betaine (betaine) or a salt thereof, glycerolphosphocholine (GPC) or a salt thereof, methylamines or a salt thereof, trimethylamine N-oxide (TMAO), a Histone deacetylase (DHAC), Vorinostat, Romidepsin, Chidamide, Panobinostat, Valproic acid), Belinostat, Mocetinostat (MGCD0103), Abexinostat (PCI-24781), Entinostat (MS-275), SB939, Resminostat (4SC-201), Givinostat (ITF2357), Quisinostat, HBI-8000, Kevetrin, CUDC-101, AR-42, CHR-2845, CHR-3996, 4SC-202, CG200745, ACY-1215, lenalidomide, ME-344, sulforaphane, or an alpha-crystallin protein or a salt thereof.

11. The composition of claim 1, further comprising an autophagy stimulator selected from at least one of: Tat-beclin1 peptide (SEQ ID NO:1), Tat-Beclin 1 D11 (SEQ ID NO:10), trehalose, trans-N,N'-(cyclohexane-1,4-diyl)bis(2-(4-chlorophenoxy)acetamide, Rapamycin, Torin-2, everolimus, temsirolimus, KU-0063794, WYE-354, AZD8055, or metformin.

* * * * *

```
                         SEQUENCE LISTING

<160> NUMBER OF SEQ ID NOS: 10

<210> SEQ ID NO 1
<211> LENGTH: 31
<212> TYPE: PRT
<213> ORGANISM: Artificial Sequence
<220> FEATURE:
<223> OTHER INFORMATION: Synthetic peptide

<400> SEQUENCE: 1

Tyr Gly Arg Lys Lys Arg Arg Gln Arg Arg Gly Gly Thr Asn Val
1               5                   10                  15

Phe Asn Ala Thr Phe Glu Ile Trp His Asp Gly Glu Phe Gly Thr
                20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic peptide

<400> SEQUENCE: 2

Tyr Gly Arg Lys Lys Arg Arg Gln Arg Arg Gly Gly Val Gly Asn
1               5                   10                  15

Asp Phe Phe Ile Asn His Glu Thr Thr Gly Phe Ala Thr Glu Trp
                20                  25                  30

<210> SEQ ID NO 3
<211> LENGTH: 450
<212> TYPE: PRT
<213> ORGANISM: Homo sapiens

<400> SEQUENCE: 3

Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
```

```
                20              25              30
Ile Leu Asp Arg Val Thr Ile Gln Glu Leu Thr Ala Pro Leu Leu Thr
                35              40              45

Thr Ala Gln Ala Lys Pro Gly Glu Thr Gln Glu Glu Thr Asn Ser
    50              55              60

Gly Glu Glu Pro Phe Ile Glu Thr Pro Arg Gln Asp Gly Val Ser Arg
65              70              75              80

Arg Phe Ile Pro Pro Ala Arg Met Met Ser Thr Glu Ser Ala Asn Ser
                85              90              95

Phe Thr Leu Ile Gly Glu Ala Ser Asp Gly Thr Met Glu Asn Leu
        100             105             110

Ser Arg Arg Leu Lys Val Thr Gly Asp Leu Phe Asp Ile Met Ser Gly
        115             120             125

Gln Thr Asp Val Asp His Pro Leu Cys Glu Glu Cys Thr Asp Thr Leu
        130             135             140

Leu Asp Gln Leu Asp Thr Gln Leu Asn Val Thr Glu Asn Glu Cys Gln
145             150             155             160

Asn Tyr Lys Arg Cys Leu Glu Ile Leu Glu Gln Met Asn Glu Asp Asp
                165             170             175

Ser Glu Gln Leu Gln Met Glu Leu Lys Glu Leu Ala Leu Glu Glu Glu
            180             185             190

Arg Leu Ile Gln Glu Leu Glu Asp Val Glu Lys Asn Arg Lys Ile Val
            195             200             205

Ala Glu Asn Leu Glu Lys Val Gln Ala Glu Ala Glu Arg Leu Asp Gln
    210             215             220

Glu Glu Ala Gln Tyr Gln Arg Glu Tyr Ser Glu Phe Lys Arg Gln Gln
225             230             235             240

Leu Glu Leu Asp Asp Glu Leu Lys Ser Val Glu Asn Gln Met Arg Tyr
                245             250             255

Ala Gln Thr Gln Leu Asp Lys Leu Lys Lys Thr Asn Val Phe Asn Ala
            260             265             270

Thr Phe His Ile Trp His Ser Gly Gln Phe Gly Thr Ile Asn Asn Phe
            275             280             285

Arg Leu Gly Arg Leu Pro Ser Val Pro Val Glu Trp Asn Glu Ile Asn
    290             295             300

Ala Ala Trp Gly Gln Thr Val Leu Leu Leu His Ala Leu Ala Asn Lys
305             310             315             320

Met Gly Leu Lys Phe Gln Arg Tyr Arg Leu Val Pro Tyr Gly Asn His
                325             330             335

Ser Tyr Leu Glu Ser Leu Thr Asp Lys Ser Lys Glu Leu Pro Leu Tyr
            340             345             350

Cys Ser Gly Gly Leu Arg Phe Phe Trp Asp Asn Lys Phe Asp His Ala
            355             360             365

Met Val Ala Phe Leu Asp Cys Val Gln Gln Phe Lys Glu Glu Val Glu
    370             375             380

Lys Gly Glu Thr Arg Phe Cys Leu Pro Tyr Arg Met Asp Val Glu Lys
385             390             395             400

Gly Lys Ile Glu Asp Thr Gly Ser Gly Ser Tyr Ser Ile Lys
                405             410             415

Thr Gln Phe Asn Ser Glu Glu Gln Trp Thr Lys Ala Leu Lys Phe Met
            420             425             430

Leu Thr Asn Leu Lys Trp Gly Leu Ala Trp Val Ser Ser Gln Phe Tyr
            435             440             445
```

Asn Lys
    450

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
gaccactctg tttccgtttc c                                             21

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
aggtctctta gatgattacc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
caccactctt gaccctgctt                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gggattgagg gtcacatcat                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
aaccgacaaa gacaccttcg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
accctagatc ccaccaggac                                               20

<210> SEQ ID NO 10
<211> LENGTH: 24

```
<212> TYPE: PRT
<213> ORGANISM: Artificial Sequence
<220> FEATURE:
<223> OTHER INFORMATION: Synthetic peptide

<400> SEQUENCE: 10

Arg Arg Arg Gln Arg Arg Lys Lys Arg Gly Tyr Gly Gly Asp His Trp
1               5                   10                  15

Ile His Phe Thr Ala Asn Trp Val
            20
```